United States Patent
Zhang et al.

(10) Patent No.: US 9,878,072 B2
(45) Date of Patent: Jan. 30, 2018

(54) BIOABSORBABLE MEDICAL DEVICE OR MEDICAL DEVICE COMPONENT AND PREPARATION METHOD THEREOF

(71) Applicant: Lifetech Scientific (Shenzhen) Co., Ltd., Shenzhen (CN)

(72) Inventors: Deyuan Zhang, Shenzhen (CN); Wenjiao Lin, Shenzhen (CN); Xiangdong Liu, Shenzhen (CN); Wenbin Wang, Shenzhen (CN)

(73) Assignee: Lifetech Scientific (Shenzhen) Co. Ltd. (CN)

( * ) Notice: Subject to any disclaimer, the term of this patent is extended or adjusted under 35 U.S.C. 154(b) by 96 days.

(21) Appl. No.: 14/391,934

(22) PCT Filed: Apr. 11, 2013

(86) PCT No.: PCT/CN2013/074065
§ 371 (c)(1),
(2) Date: Feb. 4, 2015

(87) PCT Pub. No.: WO2013/152728
PCT Pub. Date: Oct. 17, 2013

(65) Prior Publication Data
US 2015/0151027 A1    Jun. 4, 2015

(30) Foreign Application Priority Data

Apr. 12, 2012   (CN) .......................... 2012 1 0106761

(51) Int. Cl.
*A61F 2/86*    (2013.01)
*A61L 31/14*   (2006.01)
(Continued)

(52) U.S. Cl.
CPC .............. *A61L 31/148* (2013.01); *A61F 2/86* (2013.01); *A61L 27/042* (2013.01); *A61L 27/58* (2013.01);
(Continued)

(58) Field of Classification Search
None
See application file for complete search history.

(56) References Cited

U.S. PATENT DOCUMENTS

2007/0142897 A1*  6/2007  Consigny ................. A61F 2/86
                                                              623/1.15
2010/0087910 A1    4/2010  Weber
(Continued)

FOREIGN PATENT DOCUMENTS

CN          101549170 A       10/2009

*Primary Examiner* — Leslie Lopez
(74) *Attorney, Agent, or Firm* — Raymond Sun

(57) ABSTRACT

A bioabsorbable medical device or a medical device component comprises an absorbable component prepared by subjecting a prefabricated component of an iron-based raw material to ion nitriding. Substance composition inside the absorbable component changes with the depth from the surface. The absorbable component comprises at least a first part and a second part. The first part surrounds the second part. Hardness of the first part is higher than hardness of the second part. An interface exists between the first part and the second part. A crack generated in the first part is impeded by the interface when extending to the second part. On the premise of ensuring radial stand strength, the bioabsorbable medical device or medical device component and a preparation method thereof reduce wall thickness of an iron-based stand, improve a stand corrosion rate and malleability, and achieve broader adaptability.

24 Claims, 8 Drawing Sheets

(51) Int. Cl.
*A61L 31/02* (2006.01)
*A61L 27/58* (2006.01)
*A61L 27/04* (2006.01)
*C23C 8/38* (2006.01)
*C25F 3/24* (2006.01)
*C23C 8/36* (2006.01)
*C23C 8/26* (2006.01)
*C23C 8/02* (2006.01)
*C23C 8/80* (2006.01)

(52) U.S. Cl.
CPC .............. *A61L 31/022* (2013.01); *C23C 8/02* (2013.01); *C23C 8/26* (2013.01); *C23C 8/36* (2013.01); *C23C 8/38* (2013.01); *C23C 8/80* (2013.01); *C25F 3/24* (2013.01); *A61F 2210/0004* (2013.01); *A61F 2240/001* (2013.01); *A61F 2250/003* (2013.01); *A61F 2250/0019* (2013.01)

(56) References Cited

U.S. PATENT DOCUMENTS

2010/0168841 A1*  7/2010  Furst .................... A61L 27/047
                                                           623/1.42
2011/0077732 A1*  3/2011  Bayer ................... A61L 31/022
                                                           623/1.44
2011/0307051 A1*  12/2011 Atanasoska ............... A61F 2/92
                                                           623/1.16

* cited by examiner

BIOABSORBABLE MEDICAL DEVICE OR MEDICAL DEVICE COMPONENT AND PREPARATION METHOD THEREOF

TECHNICAL FIELD

The present invention relates to a bioabsorbable medical device or medical device component and a preparation method thereof, in particular to a multi-layer structure of a nitrided bioabsorbable medical device (such as an iron-based vascular stent) or bioabsorbable medical device component and a preparation method thereof.

BACKGROUND ART

In 1977, Gruentzig underwent the first case of percutaneous transluminal coronary angioplasty (PTCA), breaking through the therapy situation of drugs and surgery and creating a new era of interventional cardiology. Since the development of interventional therapy of coronary heart diseases, a percutaneous transluminal coronary angioplasty (PTCA) era, a bare metal stent (BMS) era and a drug-eluting stent (DES) era have been experienced. The vascular restenosis rate is reduced to below 10% by a drug stent from 50% of balloon dilatation alone and 20 to 30% of a bare metal stent, especially when small vascular diseases are suffered or a lesion period is longer. The advantages of the drug stent are very obvious.

The coronary stents commonly used in clinic falls into two categories: bare metal stents and drug-eluting stents. Currently, the market share of the drug-eluting stents reaches 95% in China, but in foreign countries, the market share of the bare metal stents is still 30% to 50%. This is because that although the restenosis and revascularization rates can be reduced by the DES, the existing polymer carrier drug stents still have some limitations, mainly showing late and very late stent thrombosis problems, delayed endothelial healing and late catch-up of lumen loss, and the main reason is polymer carrier-induced inflammation. The problems and the effective means for solving the problems have been widely debated in the field of international research. One research field is to develop a fully biodegradable polymer coating drug-loaded stent, and the other development field is to avoid the use of a polymer coating. i.e., a carrier free drug stent. However, since a substrate material belongs to a permanent implant, its long-term potential risks still exist.

The therapy method of infant congenital vascular stenosis (coarctation of the aorta and pulmonary stenosis) includes surgery, balloon angioplasty and stent implantation. Although surgery is a good method, it is a thoracotomy and has a big trauma; meanwhile it is difficult to solve the pulmonary branch stenosis and postoperative restenosis. The balloon angioplasty and the stent implantation, which are safe transcatheter interventional therapy methods, have advantages of less trauma and shorter hospital stay, etc.; but the balloon angioplasty leads to a higher incidence of complications, especially for babies; therefore, the stent implantation is proved to be a better choice. However, infants have further growth and development characteristics, and the non-absorbable stents implanted can cause restenosis in the late period of vascular growth; although the stent diameter can be consistent with the vascular growth by a re-expansion method, adult stents cannot be implanted into blood vessels of infants because blood vessels of infants are thinner.

Currently, the bioabsorbable vascular stent has become a research focus, and has the advantages that the ordinary stents do not have: further growth of blood vessels and the follow-up vascular surgical therapy cannot be hindered; after the bioabsorbable stent is completely absorbed by the human body, narrow blood vessels will be restored to healthy and natural normal blood vessels with a physiological vasomotor capacity; the stent can be fully absorbed until the stent disappears completely, so that the chronic injury and inflammatory reaction caused by the stent for a long term can be avoided and the late stent thrombosis is reduced and so anti-platelet drugs do not need to be taken for a long term; once the stent is completely absorbed, the stent does not have the long-term potential adverse effects on the blood vessels without increasing the surgery difficulty of re-PCI or surgical revascularization, which has a great significance, especially for the blood vessels of children in the period of growth and development.

The bioabsorbable stents mainly comprise a polymer-based bioabsorbable stent and a metal-based bioabsorbable stent. But the former has unsatisfactory biomechanical properties, and simultaneously the complexity of such stent release process is much higher than that of the conventional balloon dilatation metal stent. The latter mainly includes a magnesium alloy stent and an iron stent at present. The magnesium alloy stent cannot play an effective supporting role before revascularization due to its too fast corrosion rate; therefore, the development focus of the magnesium alloy stent lies in how to reduce the corrosion rate thereof. Pure iron applied to the bioabsorbable stents has the main disadvantages of low mechanical properties and too slow corrosion rate. In the prior art, a composite coating containing strontium or calcium, or both is prepared on the surface of bioabsorbable metal materials such as pure iron by physical vapor deposition to accelerate and control the corrosion rate of the materials. In addition, a polymer coating which can be degraded in an acidic environment is sputtered on the composite coating to further accelerate the corrosion rate of the materials. However, such a method fails to solve the problems of low mechanical properties of pure iron materials. The coating and substrate pure iron have a problem on whether both are firmly bound or not due to their non-integrated structure.

The current research mainly focuses on developing novel iron-based alloys and finding novel iron material preparation methods, or preparing an iron alloy layer on the surface of the pure iron material and modifying the pure iron material in order to solve the problems of the pure iron stents; wherein the pure iron stent is subjected to surface alloying treatment (carburizing, nitriding, and carbonitriding) to obtain a composite diffusion layer with an adjustable permeation depth, thereby improving the strength of the stent, and simultaneously accelerating the corrosion rate of the stent and shortening the absorption cycle of the stent. After the stent is subjected to surface alloying, the stent has a non-continuous diffused composite diffusion layer. By controlling the distribution, shape and depth of the diffusion layer, the yield strength and elongation can be adjusted in a wide range to achieve the strength and absorption cycle required by the stent. The composite diffusion layer comprises a solid solution that nitrogen exists in iron, and $Fe_4N$.

The bioabsorbable metal represented by pure iron and magnesium alloy can be used for manufacturing other implantable medical devices other than for manufacturing bioabsorbable vascular stents.

The vascular stent subjecting to a surface treatment method such as nitriding, carburizing or carbonitriding and then being polished in the prior art has a composite diffusion layer with the adjustable permeation depth. An unsolved technical problem is how to optimize the structure on this basis to improve the comprehensive properties (radial strength, flexibility, fatigue resistance and corrosion rate) of the absorbable stent.

The radial strength of the stent is defined herein as a pressure required when the stent radially deforms by 10%. For a coronary stent with an outer diameter of 1.6 mm, the outer diameter is dilated to 3.0 mm by a balloon generally and then the radial strength is measured. A 316L stainless steel coronary stent has a wall thickness of about 100 μm usually, and a radial strength ranging from 110 KPa to 150 KPa; the mechanical properties of cobalt-chromium alloy is slightly better than those of 316L stainless steel, and a cobalt-chromium alloy coronary stent has a wall thickness of about 80 μm usually with a radial strength ranging from 140 KPa to 185 KPa.

The blood vessels of human body usually tend to be bent or twisted, especially a vascular lesion segment. Flexibility of the stent refers to a capacity of the stent to adapt to bent blood vessels. The better the stent flexibility is, the stronger the penetration capacity of the stent through the blood vessels is. According to the finite element analysis of the stent, a wall thickness of the stent not only is a main factor affecting the stent flexibility, but also one of key parameters reflecting the comprehensive properties of the stent. Meanwhile, the wall thickness of the stent is regarded as an independent predictive factor of late lumen loss (vascular restenosis) after vascular lesions are treated by an interventional therapy, and the evidence-based medicine agrees that the restenosis rate of a thin-walled stent is lower than that of a thick-walled stent. However, the wall thickness of the stent is reduced at the expense of the loss of radial strength of the stent; therefore the wall thickness of the stent is strictly limited by clinical requirements. The commonly used coronary stents are all permanently implantable, including bare metal stents and drug-eluting stents, in which 316L stainless steel or cobalt-based alloy are usually taken as a substrate material. However, the mechanical properties of the stent depend on the substrate material and the stent structure design, i.e., the mechanical properties of the coronary stent can not be affected by drugs basically. Under the premise of ensuring the clinical therapeutic effects, the wall thickness of the current permanently implantable coronary stent can only be reduced to 65 μm, and the stent uses cobalt-chromium alloy as the substrate material. Under the same mechanical property requirements, although the wall thickness of the iron-based coronary stent is significantly less than that of the coronary stents made from other bioabsorbable materials, the wall thickness of the bioabsorbable iron-based coronary stent obtained by the prior art can only be reduced to 90 μm or so, and does not reach the minimum wall thickness of 65 μm of the permanently implantable coronary stent. The technical problem on how to reduce the wall thickness of the bioabsorbable iron-based stent as much as possible under the premise of satisfying the mechanical properties such as elongation and radial strength and improving the corrosion rate of the stent has not been solved yet by the prior art.

The iron-based material (including pure iron, steel or other iron alloys) is subjected to a surface nitriding process such as ion nitriding, so that a denser compound layer is formed on the surface of the iron-based material generally. According to the known research results, the compound layer is formed by γ' phase (mainly $Fe_4N$), or by mixing γ' phase and ϵ phase (composition change range $Fe_{2-3}N$); wherein the γ' phase accounts for 50 to 100% by weight. The nitrogen content of the γ' phase is 6 wt-% or so, and the nitrogen content of the ϵ phase is 8 to II wt-% or so; therefore, nitrogen atoms in the compound layer have a very high concentration, and are diffused to inside of the material through high temperatures. The compound layer is easily formed on the surface of the iron-based stent after the iron-based stent is subjected to surface nitriding treatment, and can greatly increase brittleness of the material; the corrosion resistance of the compound layer is much higher than that of a pure iron substrate. Therefore it is necessary to fully remove the compound layer under the premise of ensuring the properties of the stent. When the iron-based stent is prepared by a prior method, if the plasma discharge bias is too low (below 600V), the average thickness of the compound layer is generally more than 10 μm. If the temperature of the iron-based stent is too high (above 550° C.), the local compound layer on the surface of the iron-based stent extends to inside of the material in a dendritic or flaky shape, resulting in very uneven thickness of the compound layer. In the prior art, a pure iron pipe subjected to drawing and mechanical polishing is used, and the grain boundary is in a disordered high-energy state due to work hardening; meanwhile, there are higher internal residual stress inside the pipe and more defects such as dislocations, thereby providing more express channels for diffusion of nitrogen atoms; the compound layer will extend to a deep part inside the iron pipe material along the grain boundary or a dense dislocation area to show an inward dendritic morphology. The crystal defects of the surface can be significantly reduced by fully annealing the pure iron pipe, but this is not conducive to the permeation of nitrogen ions; therefore it is difficult to solve the problem. In view of the subsequent imprecise and non-uniform surface polishing treatment (the larger the thickness is removed by polishing, the more unfavorable), a compound layer with a certain thickness or higher coverage rate is possibly remained after the surface of such stent is polished; therefore, the purpose of improving the corrosion rate of the iron-based stent may not be achieved.

After being implanted into the blood vessel, the absorbable stent must maintain sufficient mechanical properties within an initial period of time (several months or longer) to adapt to the bending shape of the blood vessel and block the collapse of lesion blood vessel, and can be gradually absorbed after the vascular remodeling is stable. If the local strain of the stent exceeds a certain limit, micro-cracks will be firstly generated on the surface of a part of supporting strut or connecting part. Due to vascular pulsating and blood flow, the metal fatigue of the stent will be gradually accumulated; at this time, the micro-cracks will gradually propagate to inside from the surface of the stent to become larger cracks damaging the stent structure until the stent is partially fractured, and it is even more necessary to prevent the propagation of the micro-cracks for the thin-walled stent. Therefore, the prior art needs to be optimized to ensure that sufficient pure iron or a low-nitrogen-content area is still reserved inside the nitrided stent substrate to reduce the risks of surface crack propagation and premature brittle failure of the stent (before the vascular remodeling is stable). Hence, the ratio of the depth of a nitrided layer to the wall thickness of the stent cannot be too large.

In order to obtain a better biological tissue compatibility, the roughness of inner and outer surfaces of the coronary stent should be reduced as much as possible. The ordinary electrochemical polishing used in the prior art does not have a good polishing effect on the inner wall of the stent, and the surface roughness can only be controlled below 0.1 μm, which cannot reach a mirror bright effect (surface roughness≤0.01 μm); the stent surface can be bright and smooth when the polishing removal amount (the difference value between wall thicknesses of a polished stent and an unpolished stent) reaches 40 μm above in the prior art; thus the inherent shortcomings of imprecision and unevenness of polishing treatment are more obvious, and especially not conducive to the quality control of thin-walled coronary stents.

An important technical problem related to this is that the prior art is difficult to be used for a thin-walled pipe (wall thickness is less than 100 μm). If the original pipe wall of the stent pipe is very thin, the nitrided layer is bound to be thinner. However, in order to achieve the desired polishing effect, the prior polishing method requires a higher polishing removal amount, the compound layer closest to the surface can not only be removed, but also a part of nitrided layer can be removed, so that the remaining nitrided layer will become very thin. The thickness uniformity of the nitrided layer is limited by the prior art, the polishing removal amount of different areas of the supporting strut are not uniform enough, and the two uniformities are superimposed together, resulting in the more non-uniform thickness of the remaining nitrided layer. If the remaining nitrided layer is too thin, the nitrided layers at some parts of the supporting strut will almost completely disappear, thereby bringing serious adverse effects. The nitrided layer can effectively improve the radial strength of the stent, which is especially critical to the thin-walled stent; if the thickness of the nitrided layer is not very uniform, the mechanical properties of the various parts of the stent are very inconsistent; thus, the radial strength of the stent will not meet the design requirements. In addition, if the nitrided layer is very thin and has a non-uniform thickness, some parts of the supporting strut are slowly corroded due to less nitrogen content; thus the stent can also not meet the design requirements. By further considering the process error in actual production, the difference between distant supporting struts or connecting parts will be more obvious, and the problems of inconsistency of the above-mentioned mechanical properties or less local nitrogen content will be more serious. Therefore, the polishing process in the prior art needs to be improved so as to adapt to the thin-walled pipe with a wall thickness of less than 100 μm.

DISCLOSURE OF THE INVENTION

Technical Problems

The technical problems to be solved by the present invention are to provide a bioabsorbable medical device or a medical device component and a preparation method thereof so as to solve the problems on the conflicting characteristics among corrosion rate, radial strength, flexibility and wall thickness of the bioabsorbable medical device or medical device component in the prior art being difficult to achieve a relatively perfect balance point.

Solution of Solving the Problems

Technical Solution

The technical solution used to solve the technical problems of the present invention is to provide a bioabsorbable medical device or a medical device component, which comprises an absorbable component produced by subjecting a prefabricated component made from an iron-based raw material to ion nitriding treatment. The material composition inside the absorbable component changes with the depth from the surface. The absorbable component comprises at least a first part and a second part. The second part is surrounded by the first part. A hardness of the first part is higher than that of the second part. An interface is distributed between the first part and the second part. Cracks generated in the first part are obstructed by the interface when propagating to the second part.

As a further improvement of the present invention, the absorbable component comprises a diffusion layer which is continuously distributed from the surface, but excludes a corrosion resistant compound layer, the diffusion layer comprises a solid solution with a nitrogen content of less than 1 wt-%, and particles with a nitrogen content of more than 1 wt-%; the particles are diffused in the solid solution; the absorbable component also comprises a solid solution layer surrounded by the diffusion layer; the first part comprises the whole diffusion layer; the second part comprises the whole solid solution layer, and the diffusion layer and the solid solution layer are respectively positioned at the two opposite sides of the interface.

As a further improvement of the present invention, the absorbable component comprises a diffusion layer which is continuously distributed from the surface, but excludes a corrosion resistant compound layer, the diffusion layer comprises a solid solution with a nitrogen content of less than 1 wt-%, and particles with a nitrogen content of more than 1 wt-%; the particles are diffused in the solid solution; both the first part and the interface are distributed inside the diffusion layer.

As a further improvement of the present invention, the nitrogen content of the diffusion layer is between 1 wt-% and 3.7 wt-%.

As a further refinement of the present invention, the particles account for not more than 63% by weight percent of the diffusion layer.

As a further improvement of the present invention, the sizes of most particles are between 30 nm to 2 μm, a part having a maximum hardness of the absorbable component is distributed nearby the surface of the absorbable component and a maximum hardness does not exceed 350 HV; a hardness of each part of the diffusion layer is increased by over 50 HV compared with the hardness of the non-nitrided iron-based raw material of the prefabricated component.

As a further improvement of the present invention, the hardness of the diffusion layer is more than 220 HV and less than 320 HV, and gradually decreases with the depth.

As a further improvement of the present invention, the sizes of most particles are between 30 nm and 500 nm.

As a further improvement of the present invention, the thickness of the diffusion layer accounts for 75% to 90% of the thickness of the absorbable component.

As a further improvement of the present invention, the absorbable component further comprises a core layer surrounded by the solid solution layer; the hardness of the solid solution layer is increased by over 10 HV compared with the hardness of the non-nitrided iron-based raw material of the prefabricated component, the thickness of the diffusion layer accounts for 50% to 70% of the thickness of the bioabsorbable medical device or medical device component, and the thickness of the solid solution layer accounts for 15% to 25% of the thickness of the bioabsorbable medical device or medical device component.

As a further improvement of the present invention, the bioabsorbable medical device is an absorbable vascular stent; the absorbable component comprises a plurality of supporting struts connected to form a tubular grid, the vascular stent is produced by subjecting an iron-based pipe with a uniform wall thickness to engraving and ion nitriding treatment, and the wall thickness of the vascular stent is between 60 μm and 300 μm under the conditions of same tubular grid and wall thickness, the radial strength of the vascular stent is increased by 30% above compared with the radial strength of the non-nitrided vascular stent prefabricated by the iron-based raw material.

As a further improvement of the present invention, the vascular stent has a wall thickness of between 60 μm and 300 μm, and a mass of between 5 mg and 100 mg.

As a further improvement of the present invention, the vascular stent has a wall thickness of between 60 μm and 100 μm or between 160 μm and 170 μm.

As a further improvement of the present invention, the vascular stent has a hardness of between 280 HV and 320 HV; under the conditions of same tubular grid and wall thickness, the radial strength of the vascular stent is increased by 80% above compared with the radial strength of the non-nitrided vascular stent prefabricated by the iron-based raw material.

As a further improvement of the present invention, the electrochemical corrosion surface current density of the bioabsorbable medical device or medical device component is increased by 20% above compared with the electrochemical corrosion surface current density of the non-nitrided iron-based raw material.

Another technical solution used to solve the technical problems of the present invention is to provide a bioabsorbable medical device or a preparation method of a bioabsorbable medical device component, comprising the steps of:

1. taking pure iron or an iron alloy with an iron content of more than 99 wt-% as a raw material to be processed into a prefabricated component, the initial thickness of which is over 10 μm greater than a corresponding thickness of the medical device or medical device component:

2. cleaning to remove contaminants on the surface of the prefabricated component:

3. treating the prefabricated component in step 2 by using an ion nitriding method, the prefabricated component having a temperature of between 430° C. and 550° C. and nitriding time of between 10 minutes and 200 minutes:

4. subjecting the nitrided prefabricated component to an electrochemical polishing treatment or a chemical polishing treatment to remove more than 5 μm outer layer thickness of the prefabricated component.

As a further improvement of the preparation method of the present invention, in step 1, the prefabricated component has a surface hardness of between 165 HV and 175 HV.

As a further improvement of the preparation method of the present invention, in step 1, the thickness of the prefabricated component is 20 to 60 μm greater than the corresponding thickness of the medical device or medical device component.

As a further improvement of the preparation method of the present invention, in step 3, the current density generated on the surface of the prefabricated component by the ion nitriding method is between 0.5 mA/cm$^2$ and 0.8 mA/cm$^2$.

As a further improvement of the preparation method of the present invention, step 3 further comprises: generating a compound layer on the surface of the prefabricated component, and an average thickness of the compound layer is not more than 5 μm.

As a further improvement of the preparation method of the present invention, step 3 further comprises: generating a diffusion layer and a solid solution layer in the prefabricated component the solid solution layer is surrounded by the diffusion layer, the hardness of both the diffusion layer and the solid solution layer gradually decreases with the depth, and the hardness of each part of the solid solution layer is increased by 10 to 50 HV compared with the hardness of the non-nitrided iron-based raw material of the prefabricated component.

As a further improvement of the preparation method of the present invention, step 3 further comprises: further generating a core layer in the prefabricated component, the solid solution layer is surrounded by the diffusion layer, and the core layer is surrounded by the solid solution layer.

As a further improvement of the preparation method of the present invention, in step 3, the temperature of the prefabricated component is between 470° C. and 520° C.

As a further improvement of the preparation method of the present invention, in step 3, the ion nitriding method adopts a mixed gas of nitrogen and hydrogen, the flow ratio of nitrogen to hydrogen is between 1:2 and 1:9, and gas discharge is maintained at a pressure of between 40 Pa and 150 Pa and a bias of between 600V and 800V.

As a further improvement of the preparation method of the present invention, in the step, the flow ratio of nitrogen to hydrogen is between 1:3 and 1:7, and gas discharge is maintained at a pressure of between 50 Pa and 100 Pa and a bias of between 600V and 650V.

As a further improvement of the preparation method of the present invention, in step 4, the electrochemical polishing treatment adopts an electrochemical polishing solution prepared by uniformly mixing anhydrous acetic acid and perchloric acid with a mass concentration of 70% according to a volume ratio of 85:15.

As a further improvement of the preparation method of the present invention, in step 4, after the electrochemical polishing treatment, the chemical polishing treatment is carried out again to remove 15 to 25 μm outer layer thickness of the prefabricated component.

As a further improvement of the preparation method of the present invention, in step 4, the chemical polishing treatment adopts a three-acid system polishing solution having a temperature of between 100° C. and 180° C. and comprising the following main components of 30% to 55% of $H_3PO_4$, 20% to 45% of $H_2SO_4$. 5% to 15% of $HNO_3$ and 15% to 30% water.

As a further improvement of the preparation method of the present invention, in step 4, the time of chemical polishing treatment is between 3 seconds and 8 seconds.

Beneficial Effects of the Invention

Beneficial Effects

Compared with the prior art, the bioabsorbable medical device or medical device component provided by the present invention has the following advantages.

1. The absorbable component of the bioabsorbable medical device is provided with a multi-layer structure internally. An absorbable stent is taken as an example; the mutually contradictory characteristics of corrosion rate, radial strength, flexibility, and wall thickness of the stent can achieve a relatively perfect balance point. The technical solution of the present invention also provides a preparation method of the absorbable medical device, and determines preferred process parameters and corresponding property effects.

2. By using the preferred mixed gas flow ratio, air pressure, component temperature, bias, nitriding time and component temperature, the internal structure of the component can be controlled, the thickness of the component layer on the surface of the component is below 5 μm. Such compound layer can be completely removed by a preferred electrochemical or chemical polishing treatment. Both the inner and outer surfaces of the component can achieve a mirror bright effect just by a low polishing removal amount, and finally, the absorbable components with different internal structures can be obtained.

3. The optimized nitriding process and polishing process provided by the present invention can ensure that, with the same stent grid design and wall thickness, the absorbable iron-based vascular stent (the stent wall thickness can be reduced to 60 μm) has the supporting force comparable with that of a cobalt-chromium alloy stent. Both coronary stents and peripheral stents can achieve such effect; the radial strength of the stent is increased by 31.5% to 94.4% compared with that of a pure iron stent.

4. The present invention provides the bioabsorbable medical device or medical device component. The absorbable iron-based vascular stent is taken as an example; it comprises a multi-layer structure having a gradient property; the supporting force and flexibility of the stent can be simultaneously improved, the corrosion resistance is reduced. The incidence of fatigue cracks in the surface can be reduced; but also the propagation of surface microcracks to the inside of metal can be inhibited, so that the absorbable medical device has a higher fatigue fracture resistant property in the early period when the absorbable medical device is implanted in the human body. Because most of the fatigue cracks are firstly formed on the metal surface, the fatigue crack initiation can be prevented by improving the component surface hardness and refining grains. On the other hand, the improvement on the plasticity of inside of the component will help to inhibit crack propagation; therefore, the propagation of cracks to inside of the component can be effectively inhibited by reserving the solid solution layer or core layer with a lower hardness inside the component. After being subjected to surface nitriding, the pure iron component has a high strength and a high hardness because of the strengthening effect of second-phase particles in the diffusion layer, so that the supporting property of the stent can be effectively improved; the solid solution layer and the core layer keep a higher elongation and a good plasticity similar to pure iron.

5. The corrosion rate of the bioabsorbable medical device or medical device component according to the present invention can be increased by one time or so compared with that of a pure iron medical device, and the corrosion rate of the bioabsorbable medical device or medical device component in a simulated body fluid PBS can be increased by 180% compared with that of pure iron. When the outer surface hardness of the diffusion layer is controlled between 230 HV0.01 and 270 HV0.01, the finer the second-phase particles in the diffusion layer are, the faster the corrosion rate is. Due to the presence of a certain number of second-phase particles in the diffusion layer, the material is easily subjected to galvanic corrosion when being subjected to normal corrosion, thereby shortening the time required by human body to absorb the medical device.

BRIEF DESCRIPTION OF THE DRAWINGS

Hereinafter, the present invention will be further illustrated in conjunction with the accompanying drawings and the following embodiments, in which.

PREFERRED EMBODIMENTS OF THE PRESENT INVENTION

Figure 1:
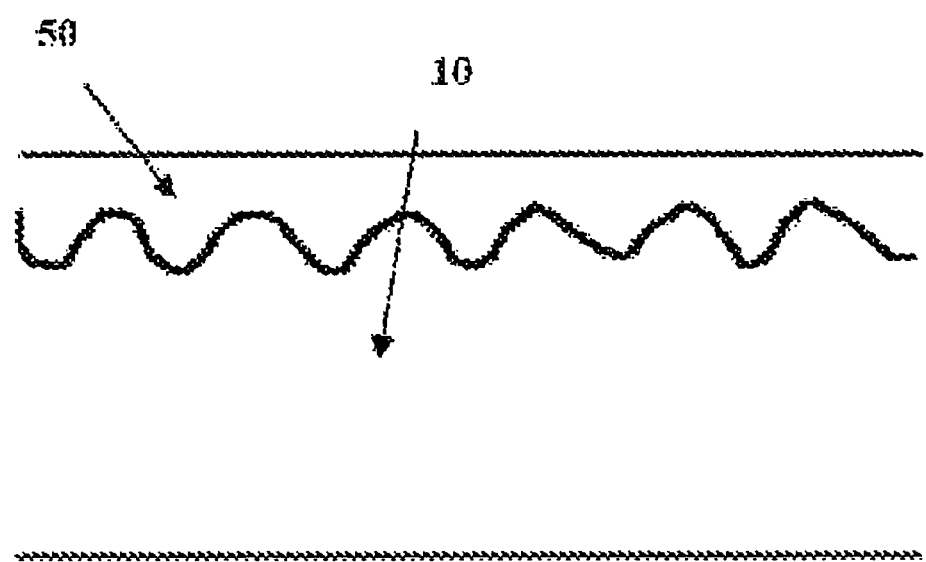
FIG. 1 is a schematic sectional view of a surface of a nitrided iron material.

The present invention is further described in detail in conjunction with the following accompanying drawings and embodiments in order to enable the objects, technical solutions and advantages of the present invention to be more clearly understood. It should be understood that the specific embodiments described herein are merely used to explain the present invention and not intended to limit the present invention.

The essence of the present invention is described in detail by mainly taking a balloon dilatation stent as an example. The stent comprising a plurality of components is produced by subjecting a round tube material to laser engraving (prefabrication) and then further treatment, and generally, a plurality of supporting struts are connected to form a whole stent grid to form a tubular side wall. The cross section of the supporting strut of the prefabricated stent is approximately rectangular, the cross section of the supporting strut of a finished stent product will lose edges and corners (more akin to an oval or a round shape), and the supporting strut of the absorbable stent is an example of an absorbable component. The thickness of the supporting strut refers to the width of the supporting strut along the diameter direction of the stent; the thicknesses of the supporting struts of the same stent, called the wall thickness of the stent, are approximately same. Flaky connecting parts may be arranged at joints of the plurality of supporting struts, and the wall thicknesses of the connecting parts and that of other parts (such as supporting struts) of the stent are the same.

In the present invention, an ion nitriding equipment in the prior art can be used to treat a pure iron prefabricated component (such as a prefabricated pure iron stent) of the medical device. The method provided by the present invention can also be used for other absorbable implantable devices (such as an occluder) or absorbable components on the implantable medical devices, and can also apply iron alloys (binary alloys or multicomponent iron alloys such as Fe—Mn alloys and Fe—Mg alloys) to optimize the properties of the absorbable medical device. Based on the method of the present invention, for the absorbable component thickness and property requirements of a general implantable medical device, the initial thickness of the prefabricated component should be 10 μm and upwards greater than the corresponding thickness of the product component, and the nitriding time of the prefabricated component is selected between 10 minutes and 200 minutes. A positive electrode of a bias power supply and a vacuum chamber of the ion nitriding equipment are connected, or a positive electrode that may hardly hinder air flow is arranged nearby a clamping table, and the prefabricated component and a negative electrode of the bias power supply are connected. A general process comprises the following steps of vacuumizing to below 2 Pa, slowly introducing a mixed gas of $N_2$ and $H_2$, and maintaining a stable air pressure selected between 40 Pa and 150 Pa, preferably a lower air pressure range such as 50 to 100 Pa. The bias power supply is turned on, so that the stent surface maintains abnormal glow discharge, and the surface of the prefabricated component is bombarded by nitrogen ions generated by gas ionization so that the temperature of the surface of the prefabricated component rises. The flow ratio of $H_2$ to $N_2$ is selected in a range of 1:2 to 1:9, wherein said $H_2$ and $N_2$ can be replaced with $NH_3$ or a mixed gas of $H_2$ and $NH_3$, and it is easy to maintain the glow discharge under substantially same bias and corresponding air pressure in accordance with the prior art. The highest temperature of the stent is limited to be 550° C. and the claming table can be heated by an auxiliary heating device to indirectly heat the whole stent, also can be preheated before turning on the bias power supply, in order that the temperature of the stent rapidly rises to 500 to 550° C. By adjusting the power of the auxiliary heating device, the temperature of the prefabricated component is stabilized, the gas discharge is also stabilized; meanwhile, the preferable range of bias is between 600V and 650V (highest up to 800V), and the surface current density of the prefabricated component is preferably between 0.5 mA/cm$^2$ and 0.8 mA/cm$^2$.

Embodiment 1

According to a well-known stent grid design, the surface of a pure iron pipe is engraved by laser to be prefabricated into a pure iron vascular stent with an outer diameter of 3.6 mm, an original wall thickness of 220 μm, and a length of 18 mm. When the stent is dilated by a balloon to 12 mm, the coverage rate of a metal grid on the surface of the stent on the side wall of the stent is 9.6% or so. Then, the stent is treated by the following steps.

First, the prefabricated pure iron stent is cleaned as follows: the pure iron stent is immersed in an electrochemical polishing solution to be subjected electrochemical cleaning for about 30 seconds at room temperature, under the conditions of introducing current of 1.6 A and voltage of 12 to 14V or so. The formula of the electrochemical polishing solution is as follows: anhydrous acetic acid and perchloric acid with a mass concentration of about 70% are uniformly mixed according to a volume ratio of 85 to 15. When other patterns are used as the stent grid design, the metal coverage rate of the surface of the stent may be changed, and meanwhile, only the current value needs to be adjusted according to the change in the metal coverage rate. Through the cleaning step, the wall thickness of the pure iron stent is reduced by 5 μm or so (the inner and outer walls are respectively thinned by 2.5 μm) in order to completely remove contaminants (including oxides) on the surface of the pure iron stent so as to ensure the effect of subsequent treatment steps. The experiment proves that, the surface of the stent is thinned by 1.5 to 3 μm to ensure that a fresh clean surface can be obtained so as to fully expose the outer surface of the pure iron substrate material; therefore, the embodiment of the cleaning step can also be replaced by an equivalent means in the prior art, which can be easily implemented by those skilled in the art.

The cleaned pure iron stent is subjected to surface nitriding treatment, wherein after being cleaned, the stent dehydrated with absolute ethyl alcohol is placed on the insulating clamping table of the ion nitriding equipment. During nitriding, a dense nitrogen-rich compound layer 50 with a certain thickness is formed on the surface of the stent, nitrogen atoms in the compound layer 50 at high temperatures are diffused to inside of the stent to form a diffusion layer 10, and the corrosion resistance of the compound layer 50 is much stronger than that of the diffusion layer 10 with less nitrogen content. A local cross-sectional view of the stent is shown in FIG. 1. As the stent is made from a polycrystalline metal material, in which irregular grain boundaries are distributed, the nitrogen atoms (ions) nearby the outer surface of the compound layer 50 more easily permeate into the diffusion layer 10 from the vicinity of the grain boundaries to form a nitride, resulting in an interface between the compound layer 50 and the diffusion layer 10 being pushed inwards. The interface undulatiesin a hill shape. The concentration of nitrogen atoms in the compound layer 50 is relatively high, but the concentration of nitrogen atoms in the diffusion layer 10 is much lower; therefore, the nitrogen atoms inevitably permeate from the compound layer 50 to inside of the diffusion layer 10. The distribution of the nitrogen atoms depends on concentration gradient, diffusion coefficient, temperature and time. The following parameters are preferably selected in the embodiment: the stent temperature being between 500° C. and 520° C., the bias being 600V or so, the flow ratio of nitrogen to hydrogen being 1:3, the air pressure being 60 Pa, the nitriding treatment time being 30 minutes, and the average thickness of the compound layer 50 formed on the surface of the stent being 2 μm or so. The concentration of reactive nitrogen ions (nitrogen potential) is appropriately reduced, for example, the flow ratio of nitrogen to hydrogen is adjusted and other parameters remain unchanged, so that the formation of the compound layer 50 and the thickness thereof can be effectively controlled. Moreover, the nitrogen ions can obtain higher kinetic energy at a higher bias, and meanwhile, the surface sputtering effect produced by the nitrogen ions on the compound layer 50 is more obvious, so that the outer surface of the compound layer 50 is continuously eroded. Therefore, a lower flow ratio of hydrogen to nitrogen (1:3 to 1:5) together with a higher bias (600 to 650V) contribute to inhibit the generation or thickening of the compound layer 50. When the bias is increased, the kinetic energy of nitrogen ions reaching the surface of the stent is increased, the ion bombardment heating effect is enhanced, so the power of the auxiliary heating device is correspondingly reduced in general in order to keep the temperature of the stent unchanged. Under the premise of maintaining the temperature of the stent between 500° C. and 550° C. the power of an auxiliary heating power supply is reduced, and the bias is appropriately increased to 700V to 800V (under this condition, the surface current of the stent is too large which may be apt to generate an electric arc to damage the stent), so that the thickness of the resulting compound layer 50 will be thinner and more uniform.

Figure 2:
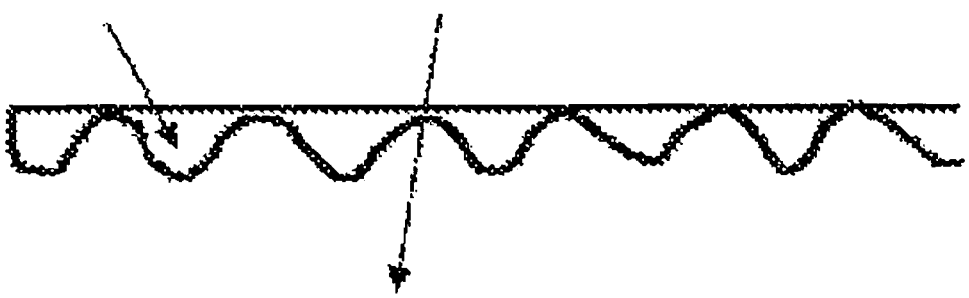
FIG. 2 is a schematic sectional view obtained after the surface shown in FIG. 1 is polished for a period of time.
Figure 3:
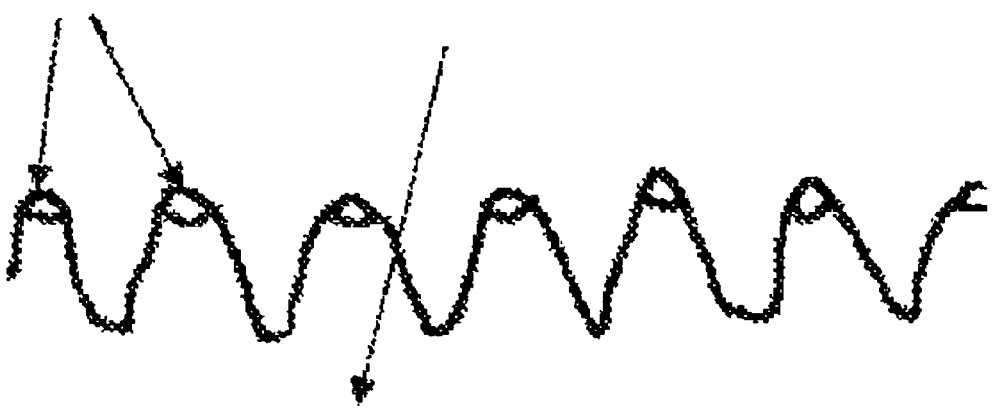
FIG. 3 is a schematic sectional view obtained after the surface shown in FIG. 2 is further polished.
Figure 4:
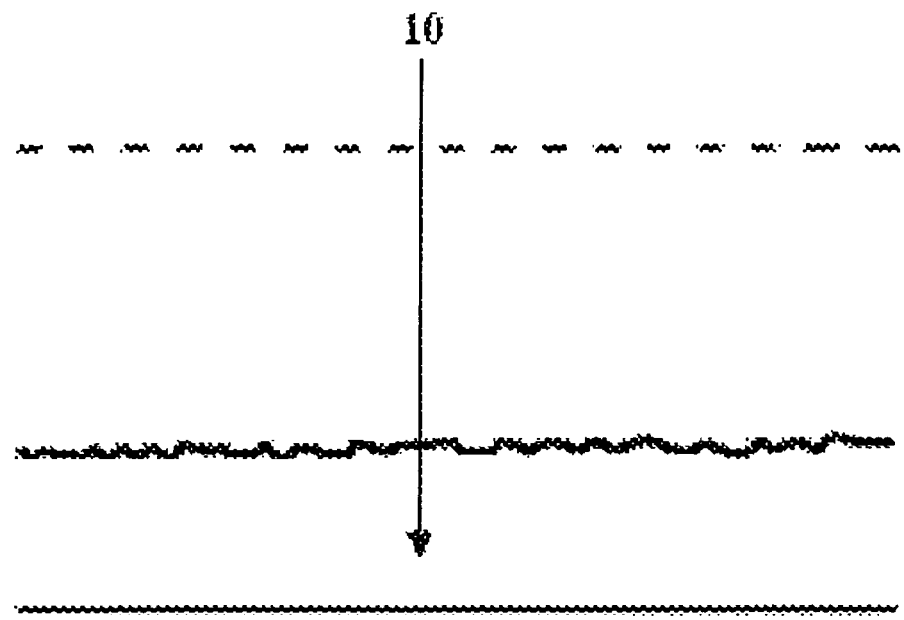
FIG. 4 is a schematic sectional view obtained when the nitrided iron material is polished to an extent meeting requirements.

After being subjected to nitriding treatment, the stent is then subjected to polishing treatment in order to completely remove the compound layer 50 and ensure that the surface of the stent is smooth and clean. The stent is placed in the electrochemical polishing solution having the aforementioned formula at a temperature of between 20° C. and 25° C. a current of 2.8 A, and a voltage of 20 to 23V or so. In this process, it is best to change the electrode clamping direction of the stent so as to ensure that the wall thickness of each part of the stent is uniformly removed. The electrochemical polishing process is divided into three stages. At the first stage, a part of the thickness of the compound layer 50 is uniformly removed until the thinnest part of the compound layer 50 is rightly and completely corroded, and a protruding part of the interface of the compound layer 50 still coexisted with the diffusion layer 10, as shown in FIG. 2. At the second stage, the polishing treatment continues, the remaining compound layer 50 is gradually thinned with pores being formed, which further becomes a discontinuous island shape to be continuously shrunk; meanwhile, the diffusion layer is corroded more quickly compared with the compound layer 50 due to its poor corrosion resistance, and the exposed outer surface of the diffusion layer 10 is preferentially corroded. As a result, compared with the outer surface of the remaining compound layer 50, the outer surface of the diffusion layer 10 is locally inwards sunken to result in the outer surface of the stent becoming very unsmooth, as shown in FIG. 3. At the third stage, after the remaining compound layer 50 is completely removed, there remains only the uneven diffusion layer 10 on the surface of the stent; because the protruding part of the diffusion layer 10 preferentially continues to be corroded compared with a sunken part, the outer surface of the stent is gradually restored to be smooth until a required surface roughness (still unsmooth from microscopic view) is reached, as shown in FIG. 4. It can be seen that the final removal amount by the electrochemical polishing treatment must be much greater than the maximum thickness of the compound layer 50 due to a great difference between corrosion resistances of the compound layer 50 and that of the diffusion layer 10. Experimental results show that, the total thickness (removal amount) of the stent's surface removed by electrochemical polishing should be at least 20 μm in order that the compound layer 50 with an average thickness of about 5 μm is removed, an approximate mirror-like polishing effect is realized, and the surface roughness Ra is less than 0.01 μm. If 20 μm thickness of the inner wall surface and 20 μm thickness of the outer wall surface of the vascular stent are removed respectively, the actually removed thickness is 40 μm; that is to say, the wall thickness of the pure iron pipe should be greater by at least 40 μm than the wall thickness of a finished stent product in order that the mirror-like effect can be achieved by the electrochemical polishing.

In said embodiment, the wall thickness of the stent is expected to be 170 μm, the wall thickness of the cleaned stent before nitriding is reduced to 215 μm, and then after nitriding, 45 μm thickness (the inner and outer walls are respectively thinned by 22.51 μm) should be removed by using electrochemical polishing treatment, thus the polishing time is set to be 110 to 120 seconds. Obviously, the polishing treatment is not only limited to be oriented in a direction perpendicular to the pipe wall of the stent, and about 45 μm thickness of each component of the stent in the direction in parallel with the pipe wall of the stent is also removed. Because the polishing treatment is simultaneously carried out in opposite two-sided directions, the actually removed thickness is respectively 22.5 μm at each side. If the second stage of the above-mentioned electrochemical polishing treatment is replaced by a chemical polishing method, the corrosion rates of both the compound layer 50 and the diffusion layer 10 will be significantly increased and the difference between the two corrosion rates will be decreased; so it will take only a few seconds to remove about 10 μm wall thickness, and the depression in the outer surface of the diffusion layer 10 shown in FIG. 3 will become relatively shallow; the formation process of unsmoothness of the surface of the stent in the above-mentioned second stage will be inhibited to be the minimum level, and correspondingly, the required removal amount of the diffusion layer 10 in the third stage will be much less; the removal amount of the whole polishing process can be reduced, the polishing time is shortened accordingly, and a thinner pure iron pipe can be selected. For example, in order that the total removal amount of the polishing treatment in the wall thickness direction is reduced to 25 μm and the polishing time is shortened by about half to obtain a stent with a wall thickness of 170 μm, a pure iron pipe with a wall thickness of 200 μm can be used; accordingly, the production efficiency is improved and the production cost is reduced. After the polishing treatment is finished, the stent is taken out, ultrasonically cleaned in purified water and then naturally dried; preferably, the stent can also be ultrasonically cleaned in absolute ethyl alcohol for 10 minutes in order to avoid the surface of the stent from being oxidized by moisture. Preferably, the stent is firstly cleaned by an alkaline solution before being cleaned by the absolute ethyl alcohol and the polished stent is placed in a sodium hydroxide solution with a weight percentage of 2% to 8% to be cleaned for about 5 minutes. It is observed under a microscope that the surface roughness Ra of the polished stent could reach 0.01 μm below.

Figure 5:
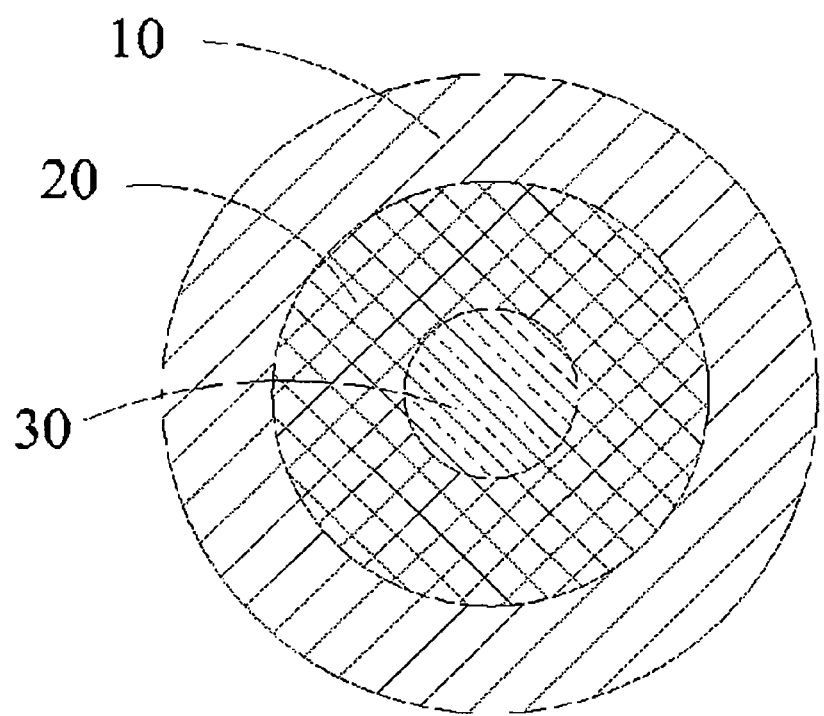
FIG. 5 is a schematic sectional view of a supporting strut of a vascular stent produced in an embodiment 1.

As a preliminary example, the cross section (simplified as a round shape) of a supporting strut of the stent from which the compound layer 50 is completely removed is shown in FIG. 5, as a specific surface nitriding effect, there exists the diffusion layer 10, the solid solution layer 20 and the core layer 30 which are successively positioned from outside to inside, the peripheral diameter (i.e., the contour diameter of the cross section of the supporting strut) of the diffusion layer 10 is equivalent to the wall thickness of the stent, the solid solution layer 20 is surrounded by the diffusion layer 10, and the core layer 30 is surrounded by the solid solution layer 20. In fact, the cross-sectional contour of any part of the vascular stent can also be in rectangular, trapezoidal, oval shapes. etc. . . . . . The nitriding and polishing respectively are inwardly and simultaneously carried out in an orientation perpendicular to the outer surface substantially, so that the boundary shapes of the diffusion layer 10, the solid solution layer 20 and the core layer 30 should respectively be similar to the contour of the cross section. It is obviously effective by analogy of the cross sections of other shapes according to the preliminary example and principles and effects thereof. The surface nitriding treatment induces regions inside the iron-based medical device differing in their micro-hardness, resulting in such regions differing in their technical effects; that is to say, the relative range of micro-hardness values of the diffusion layer 10, the solid solution layer 20 and the core layer 30 respectively meet preset conditions. The micro-hardness is measured by a Vickers hardness test with specific reference to GB/T 11345-2005; however, the stent is too small to bear a usually required test force of 0.3 kg force (2.94N), so the test force is reduced to 0.01 kg force (0.098N). In the embodiment, the raw material of the stent is a pure iron pipe formed by drawing, of which the average value of Vickers micro-hardness values is about 170 HV0.01 (a micro-hardness value measured by exerting 0.01 kg force on a sample surface and holding for 15 seconds), and of which the actual hardness value should be between 165 HV0.0 and 175 HV0.01. The hereinafter called micro-hardness of the pure iron pipe refers to an average value of a plurality of measured samples, and the micro-hardness of the pure iron pipe subjected to cold hardening during drawing molding is slightly higher than that of the annealed pure iron material (80 to 140 HV0.01).

Wherein, the core layer 30 is furthest from the outer surface of the diffusion layer 10, and very few nitrogen atoms can be diffused to the core layer 30 under the set parameter conditions; therefore, the composition of the core layer 30 is similar to that of the original pure iron pipe, the difference value between the micro-hardness of each part of the core layer 30 and that of the pure iron pipe is less than 10 HV0.01, and the hardness of a part closer to the center of cross section is lower. The plasticity of the material is quantitatively characterized by an elongation and a reduction thereof in general, and the elongation of the core layer 30 approximates to that of the original pure iron pipe (with elongation of 30% to 50%), and therefore, the core layer 30 behaves a good plasticity similar to the pure iron pipe, and it is very conducive to the prevention of stent surface cracks from propagating to the inside of the core layer 30. The main way of metal plastic deformation on a micro level is slippage. The more easily the slippage is generated, the better the plasticity is. Such slippage will result in the formation of steps on the surfaces of crystals, which makes the atoms nearby the steps keep a binding force with each other, so as to prevent from the generation of the surface cracks. For a stent with a larger wall thickness, such as a peripheral vascular stent, the plasticity of the core layer 30 is particularly important to prevent fatigue fracture of the stent.

The solid solution layer 20 is located between the diffusion layer 10 and the core layer 30, where a certain amount of nitrogen atoms have diffused into iron crystals to form approximately saturated solid solutions, or unsaturated solid solutions (having not reached saturated solid solubility at room temperature), so that the hardness thereof is significantly improved. The difference value between the micro-hardness of any part of the solid solution layer 20 and that of the pure iron pipe is between 10 HV0.01 and 50 HV0.01, and the hardness of the solid solution layer 20 also decreases with the depth, i.e., the hardness of a part closer to the center of cross section is relatively lower. The elongation of the solid solution layer 20 also approximates to that of the original pure iron pipe, which is conducive to prevent the stent surface cracks from propagating to inside of the solid solution layer 20.

The diffusion layer 10 is located on the periphery of the supporting strut cross section, into which a large number of nitrogen atoms have been diffused at a high temperature, and its saturated solid solubility of the nitrogen atoms is far more than that of nitrogen atoms in the iron crystal. In the nitriding process until cooled to room temperature, the hardness of the diffusion layer 10 is significantly increased induced by the phase change therein, and the difference value between the micro-hardness of any part of the diffusion layer 10 and that of the pure iron pipe is more than 50 HV0.01. If the micro-hardness of the non-nitrided pipe is 170 HV0.1, the micro-hardness of the diffusion layer 10 is preferably in a range of 220 to 280 HV0.01, and the highest hardness value occurred nearby the surface. The diffusion layer 10 is formed with the nitrogen-rich second phase diffusely distributing in a granular shape in a first phase region; wherein the first phase is saturated solid solutions or approximately saturated solid solutions formed by the nitrogen atoms diffusing into the iron crystals, of which the nitrogen content is less than 1 wt-% (generally less than 0.1 wt-%), and with the first phase being continuously filled in the whole region of the diffusion layer 10; the second phase comprising γ' phase ($Fe_4N$-based) and/or α" phase ($Fe_{16}N_2$), the nitrogen content of the second phase is more than 1 wt-%, the nitrogen content of the γ' phase can be up to 6 wt-% or so, the nitrogen content of the α" phase can be up to 3 wt-% or so, and the second phase accounts for not more than 63 wt-% of the diffusion layer 10. According to the law of diffusion, the concentration of nitrogen atoms in the diffusion layer 10 decreases as the increase of the depth (distance) from the surface to inside, and the number of the second phase precipitating from the first phase also decreases as the increase of the depth. Meanwhile, the diffused second-phase particles can improve the whole hardness of the material. Therefore, the hardness and plasticity of the diffusion layer 10 are gradually changed with the gradient, with the hardness gradually decreasing and the plasticity is increasing from outside to inside, and the stress is gradually released layer by layer, which plays a role in blocking crack propagation to a certain extent. At this time, a part, closer to the surface of the stent, of the diffusion layer 10 has a higher hardness, and a part, farther (deeper) from the surface of the stent, of the diffusion layer 10 had a lower hardness; in fact, the lower-hardness part is surrounded by the higher-hardness part. The cracks generated in the vicinity of the surface of the stent will propagate to the inside; however, certain initial stress is gradually released due to the hardness gradient. The cracks propagating from the higher-hardness part to the lower-hardness part will cease at a certain position, which can be regarded as an interface between the higher-hardness part and the lower-hardness part; therefore, a further propagation of cracks is obstructed by the interface. Meanwhile, as the outer surface of the diffusion layer 10 has the highest hardness, the initiation of surface microcracks can be effectively prevented.

In the embodiment, by means of nitriding with selected stent temperature of between 500° C. and 520° C. or so, the flow ratio of nitrogen to hydrogen of 1:3, the air pressure of 60 Pa and the bias of about 600V, and the polishing treatment implementing 30 minutes after such nitriding; the diffusion layer 10 shown in FIG. 5 is formed, with the hardness value of the outer surface of 260 HV0.01 or so and the size of second-phase particles therein of generally 30 nm to 2 μm; wherein the electrochemical corrosion current density of the diffusion layer 10 in the simulated body fluid PBS is about 22 μA/cm$^2$ which is more than two times higher than that of 10 μA/cm$^2$ of the pure iron stent (untreated by the method of the embodiment). Preferably, by means of nitriding with the stent temperature reduced to 500° C. or so, the flow ratio of nitrogen to hydrogen reduced to 1:5 to 1:7, the air pressure remaining 60 Pa and the bias remaining about 600V; the diffusion of the nitrogen atoms together with the agglomeration and growth of second-phase particles will be slowed down. As a result, the nitrogen content of the diffusion layer 10 is in a preferable range of between 1.0 wt-% and 3.7 wt-%, the size of a large number of fine and diffused second-phase particles is basically in a preferable range of between 30 nm and 500 nm, and the current corrosion density of the diffusion layer 10 in the simulated body fluid PBS is increased to 26 μA/cm$^2$ or so. If the nitrogen content of the diffusion layer 10 is too low (less than 1.0 wt-%), the number of the formed second phase is too few, thus a micro-galvanic corrosion only can work in a small scattered range, and the corrosion rate is not much improved compared with that of the pure iron. If the nitrogen content of the diffusion layer 10 is too high (greater than 3.7 wt-%), and the second phase particles with size more than 500 nm account for a significant proportion, as a result, the hardness of the outer surface of the diffusion layer 10 is higher than 350 HV0.01 and the galvanic corrosion rate of the outer surface of the diffusion layer 10 is relatively low instead; therefore, the surface hardness of the diffusion layer 10 should be not more than 350 HV0.01 and the hardness should gradually decrease towards the inside. As the second-phase particles may be difficulty corroded, more large-size second-phase particles will eventually hinder the penetration of corrosion. The corrosion rate of the iron-based stent is greatly improved by the preparation method and preferable parameters provided by the embodiment; therefore, the required time taken by the human body to absorb the stent is substantially shortened, which is particularly important to the peripheral vascular stent with a larger specification (comprising outer diameter and wall thickness).

Because the micro-hardnesses of the solid solution layer 20 and the core layer 30 are both far lower than that of the diffusion layer 10, if the volume ratio of the solid solution layer 20 and the core layer 30 accounting for the total supporting strut is too large, it is unfavorable to improve the radial strength of the stent. On the other hand, the outer surface of the diffusion layer 10 has a higher micro-hardness, thus helping to prevent micro-crack initiation; however the diffusion layer 10 has a poorer plasticity, thus micro-cracks having been formed on the outer surface are apt to propagate to the inside. If the volume ratio of the diffusion layer 10 accounting for the total supporting strut is too large, the fatigue resistance of the stent may be reduced. In order to take into account both the radial strength of the stent and the fatigue resistance thereof, together with a better inhibitory effect against the surface micro-crack initiation and the inward propagation of micro-cracks, the preferable ratio of the thickness (an average distance from outer surface to inner-side boundary) of the diffusion layer 10 obtained in the embodiment to the radius of the supporting strut is 53% or so, the preferable ratio of the thickness (an average distance from outer-side boundary to inner-side boundary) of the solid solution layer 20 to the radius of the supporting strut is 20% or so, the preferable ratio of the thickness (an average distance from the outer-side boundary to the center) of the core layer 30 to the radius of the supporting strut is 27% or so, herein the radius of the supporting strut is a half of the wall thickness of the stent. After the stent in the embodiment is dilated by the balloon to 12 mm, the radial strength of the stent is measured to be 66 KPa which is increased by 46.7% compared with the 45 KPa radial strength of a pure iron stent (untreated by the method of the embodiment) with the same shape and size (wall thickness being also 170 μm).

The stent temperature during nitriding is a very important parameter which determines the diffusion rate of nitrogen atoms. And the nitriding time directly affects the thicknesses of the diffusion layer 10 and the solid solution layer 20 respectively. In the present embodiment. If the nitriding temperature and the nitriding time are kept unchanged respectively, the flow ratio of nitrogen to hydrogen is reduced to 1:5, and simultaneously the bias is increased to 650 to 700V alternatively the air pressure is increased to 65 to 75 Pa, so that the nitriding current density is still maintained basically unchanged, and thus a structure and a property effect similar to that shown in FIG. 5 can be still obtained. If the flow ratio of nitrogen to hydrogen is further reduced to 1:7, while the bias is being increased to 750 to 800V alternatively the air pressure is being increased to 120 to 130 Pa, the nitriding current density may not change much, thus a structure and a property effect similar to that shown in FIG. 5 can also be obtained. When the air pressure exceeds 150 Pa, even if the flow ratio of nitrogen to hydrogen is reduced to 1:9, the stent surface current density is still too large; the temperature of the stent rapidly increases due to its very small mass; accordingly, the required stent temperature cannot be maintained even if the auxiliary heating device is turned off. Therefore, the upper limit of the air pressure is 150 Pa. The maximum value of the flow ratio of nitrogen to hydrogen may be 1:2 and the air pressure can be reduced to about 40 Pa; at this time, the concentration of nitrogen ions with chemical activity approximates to the maximum limit (nitrogen potential is higher). The surface current density of nitriding is high, easily resulting in nonuniform glow discharge on the surface of the stent. And the local stent temperature may be high, so the lower limit of the air pressure is 40 Pa.

Figure 6:
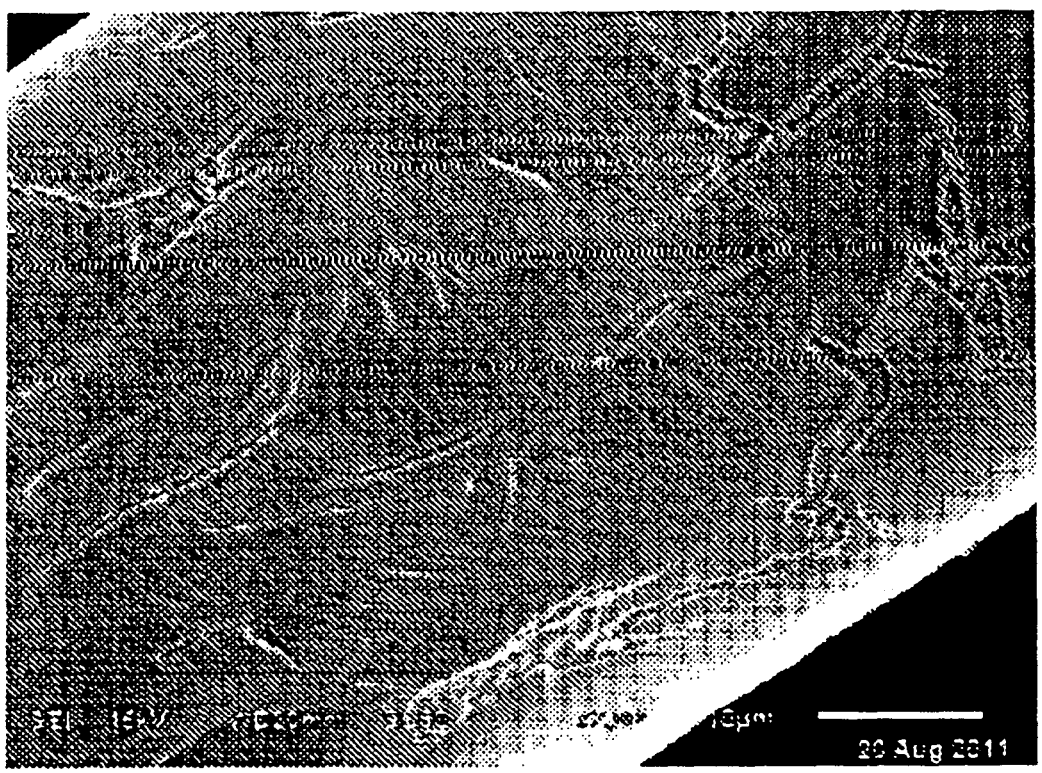
FIG. 6 is an electron microscopic photograph of a surface of a supporting strut when the vascular stent in the embodiments of the present invention is excessively dilated by 20% by a balloon (micro-cracks are limited in the surface)

The cross section of the supporting strut of the iron-based stent obtained by using the method and the parameter range provided by the embodiment is substantially shown in FIG. 5, which is preferably characterized with the diffusion layer 10 accounting for 50% to 70% of the total thickness (or the radius of supporting strut) and the solid solution layer 20 accounting for 15% to 25% of the total thickness (or the radius of supporting strut), so that the initial corrosion rate, fatigue resistance and radial strength of the stent can be significantly optimized, thereby being favorable for reducing the risk of stent fracture caused by inward propagation of surface micro-cracks due to sudden dilatation and bending fatigue of the stent. FIG. 6 shows a supporting strut of the stent observed under an electron microscope. The originally designed stent should be dilated by the balloon to be with an outer diameter of 3 mm, but here, the stent is excessively dilated to be with the outer diameter of 3.6 mm, so that micro-cracks are generated on the outer surface after a stress is applied to the stent, but do not directly propagate to inside of the supporting strut. A lot of slip bands generated on the outer surface of the supporting strut indicate that a typical plastic deformation has occurred, and the micro-cracks only tear along the outer surface. Because of the better plasticity of the core layer 30 and the solid solution layer 20, and the hardness gradient and the moderate surface hardness (not more than 280 HV0.01) of the diffusion layer; the surface micro-cracks will not propagate to inside of the supporting rod, so as to effectively reduce the risk of supporting strut fracture caused by fatigue crack propagation. That is to say, the diffusion layer 10 is a higher-hardness part, and the solid solution layer 20 is a lower-hardness part, the solid solution layer 20 is surrounded by the diffusion layer 10 and such two parts are separated by an interface. Based on the foregoing reasons, when the cracks in the diffusion layer 10 are propagating to the solid solution layer 20, the cracks will be blocked by the interface to stop propagating.

Embodiment 2

According to a well-known stent grid design, the surface of a pure iron pipe is engraved by laser to be prefabricated into a pure iron vascular stent with an outer diameter of 1.6 mm, an original wall thickness of 100 μm, and a length of 18 mm. When the stent is dilated by the balloon to 3 mm, the coverage rate of a metal grid on the surface of the stent to the side wall of the stent is 13% or so. Then, the stent is treated by the following steps.

The cleaning step described in embodiment 1 is applied, but with the current of 0.7 A instead, the voltage between 8V and 10V or so, and the electrochemical cleaning time of 15 seconds instead; as a result, a cleaning effect similar to embodiment 1 is obtained. Alternatively, as the current is increased to 0.9 A, the electrochemical cleaning time is reduced to 10 seconds and the removed amount is about 5 μm (the inner and outer walls are respectively thinned by 2.5 μm). Ion nitriding treatment is carried out after cleaning, and the ion nitriding equipment and a part of parameters are similar to that of embodiment 1. The parameters different from that of embodiment 1 are as follows: the stent temperature being between 470° C. and 500° C. the air pressure being 55 Pa, and the thickness of the compound layer 50 formed on the surface of the stent being 2 μm or so.

Figure 7:
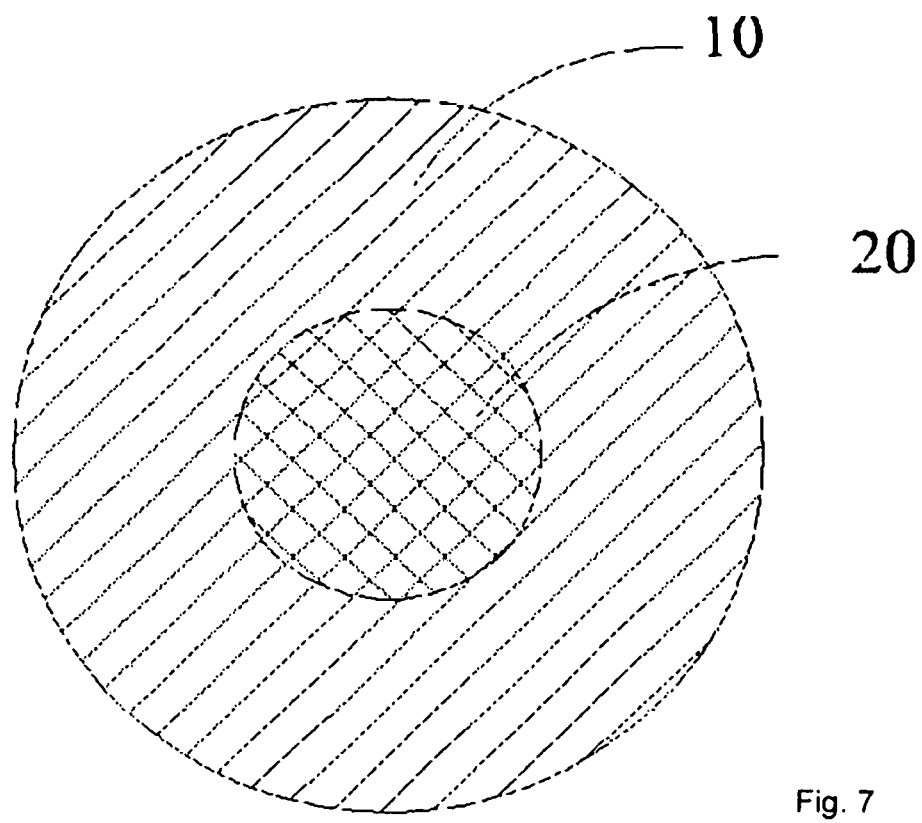
FIG. 7 is a schematic sectional view of a supporting strut of another produced vascular stent.

After subjected to nitriding treatment, the stent is further subjected to polishing treatment in order to completely remove the compound layer 50. The cross section of the supporting strut of the stent is shown in FIG. 7, and the stent surface is ensured to be smooth and clean. However, since the original wall thickness of the coronary stent is very thin, in order to ensure that a certain thickness exists for the diffusion layer 10 and the solid solution layer 20, the desired surface roughness must be obtained by a relative lower polishing removal amount. Therefore, a two-step polishing method is applied in the embodiment, wherein, first by utilization of the advantages of an electrochemical polishing which has uniformity, and is easy to be controlled but hardly leads to the excessive local polishing, and then by utilization of the advantages of a chemical polishing with a low removal amount, high polishing efficiency, and obvious leveling and brightening effects within a short time, so that an approximate mirror-bright-like polishing effect is obtained by about 20 μm of removed amount in the wall thickness direction (inner and outer walls are respectively thinned by 10 μm), and the mirror-bright-like polishing effect is obtained by the removed amount of not exceeding 30 μm. The first-step polishing is performed as follows. The stent is dipped into an electrochemical polishing solution formed by uniformly mixing anhydrous acetic acid and perchloric acid with a mass concentration of 70% according to a volume ratio of 85:15 and is being polished for 30 seconds at a temperature between 20° C. and 25° C., with a current of 0.7 A and a voltage of about 8 to 10V. In this process, it is better to change the electrode clamping direction of the stent so as to ensure that the wall thickness of each part of the stent can be uniformly removed. Then the stent is taken out and dipped in a sodium hydroxide solution with a weight percent of 2% to 8% to be cleaned for 5 minutes, and then ultrasonically cleaned in absolute ethyl alcohol for 10 minutes. Then the second-step polishing treatment is performed, i.e., chemical polishing. Preferably, a three-acid system polishing solution with major components of phosphoric acid, sulfuric acid and nitric acid, comprises 30% to 55% $H_3PO_4$. 20% to 45% of $H_2SO_4$, 5% to 15% of $HNO_3$ and 15% to 30% water. Phosphoric acid, sulfuric acid and nitric acid with appropriate concentration (weight percentage) are uniformly mixed according to an appropriate volume ratio to be prepared into such three-acid system polishing solution within the above-mentioned component range. In the embodiment, about 80% by mass of phosphoric acid, about 90% by mass of sulfuric acid, and about 60% by mass of nitric acid are mixed according to a volume ratio of 5:3:2 to be prepared into the three-acid system polishing solution. The stent is immersed in the three-acid system polishing solution and being polished for 4 to 6 seconds at a temperature of 120° C. (selected between 100° C. and 180° C.), and then the stent is taken out to be ready for cleaning. Although the nitric acid has very high volatility at higher temperature, the composition ratio of the three-acid system polishing solution is still maintained within the above-mentioned effective range because each polishing time of the stent is very short. A better cleaning method can be used here. For example, the polished stent is cleaned with purified water and then ultrasonically cleaned in absolute ethyl alcohol for 10 minutes. Preferably, the stent is cleaned in an alkaline solution before being cleaned in the absolute ethyl alcohol. i.e., the polished stent is placed in the sodium hydroxide solution with a mass concentration of 2% to 8% to be cleaned for 5 minutes or so. In order that the surface roughness Ra can reach below 0.01 μm, only about 20 μm of a wall thickness is needed to be removed by using the two-step polishing; the removed amount with the method is reduced by more than a half compared with that with a single-step electrochemical polishing, which is very favorable for optimizing the process quality of the stent. According to the need, the first-step polishing time is set to 25 to 35 seconds, and the second-step polishing time is set to 3 to 8 seconds. The removed wall thickness can be controlled between 15 μm and 25 μm (including both inner and outer walls) by precisely selecting appropriate polishing time in two steps, or adjusting the concentration and temperature of the three-acid system polishing solution in the abovementioned range.

Figure 9:
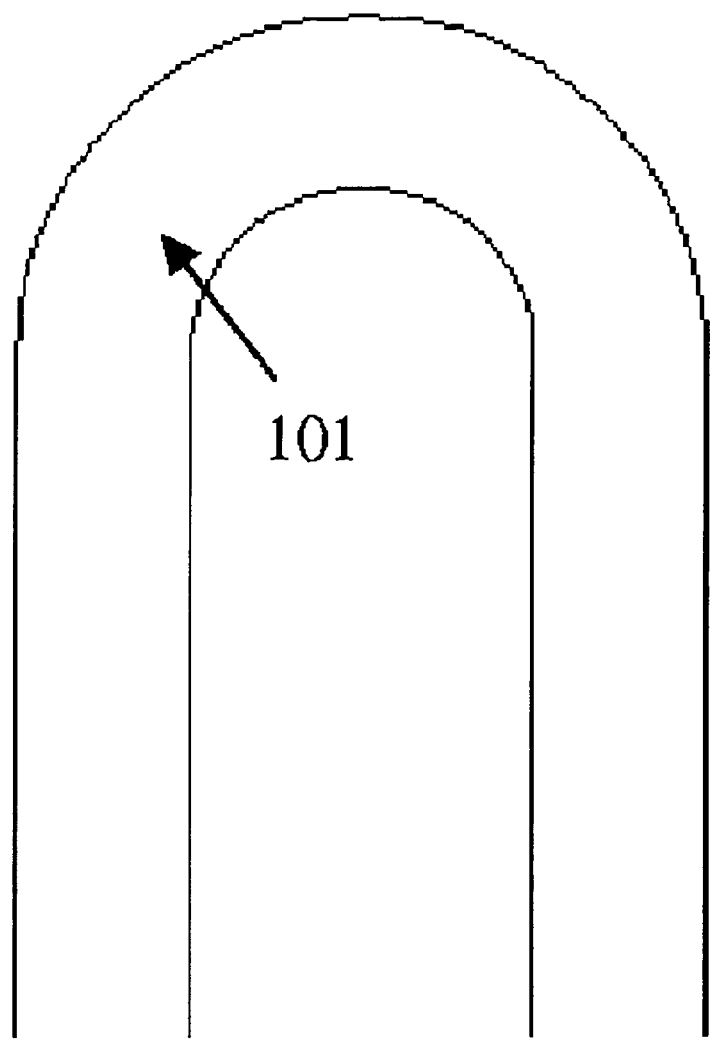
FIG. 9 is a schematic view of a slit formed by locally bending the vascular stent.
Figure 10:
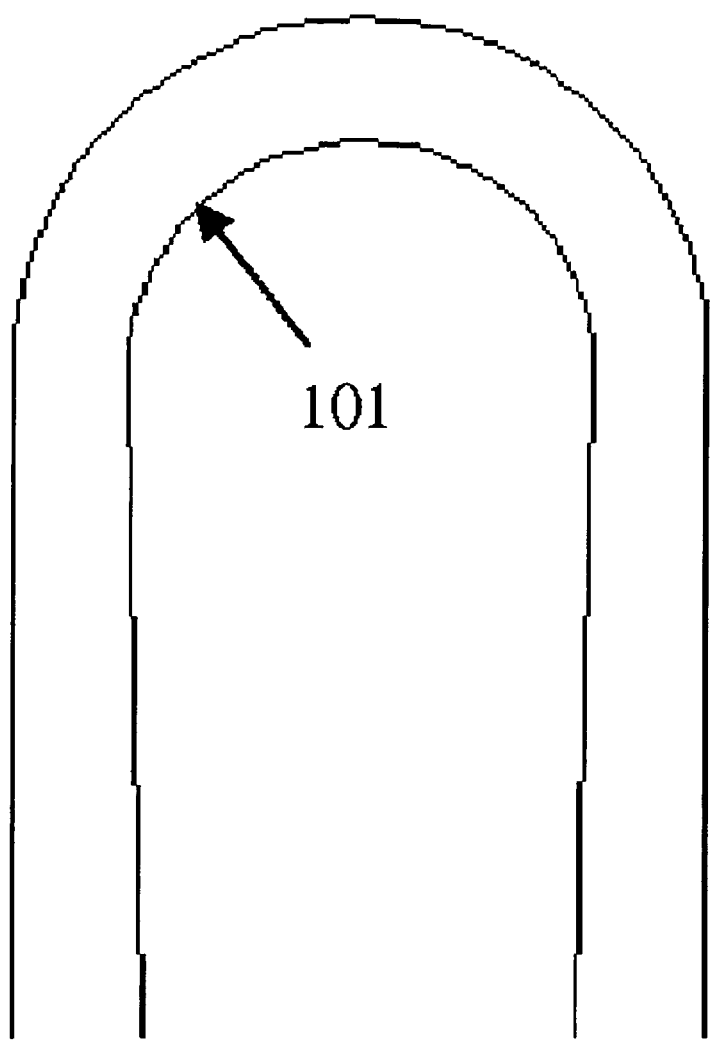
FIG. 10 is a schematic view of a uniformly corroded slit of the vascular stent shown in FIG. 9.
Figure 11:
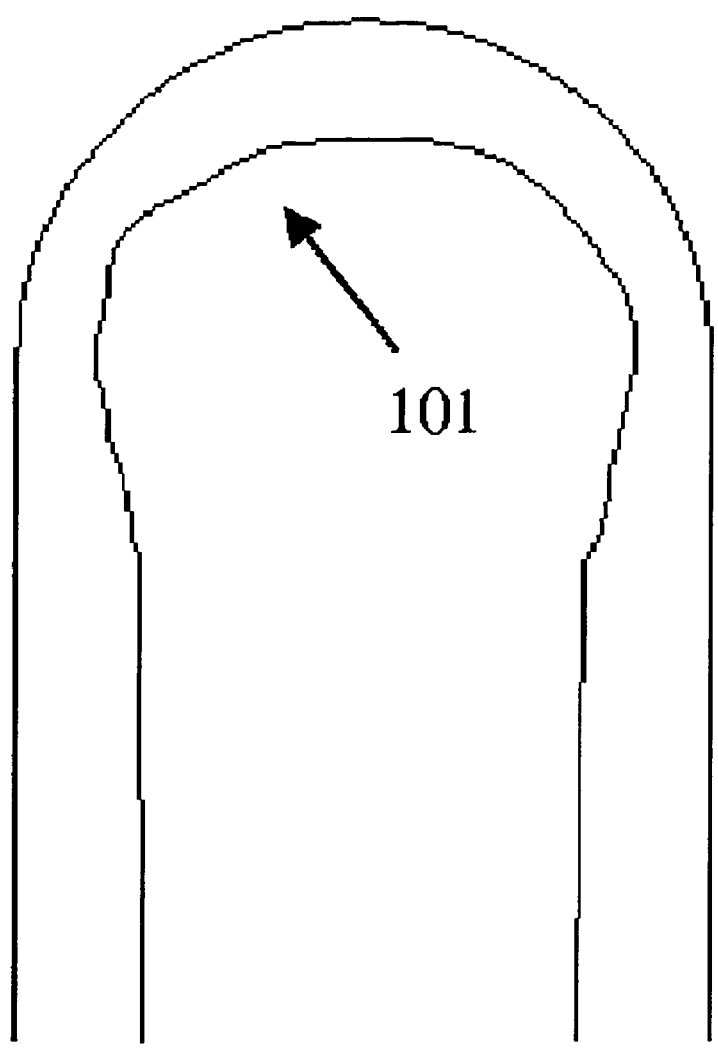
FIG. 11 is local shape distortion caused by subjecting the slit in FIG. 9 or FIG. 10 to non-uniform corrosion.

If only the chemical polishing treatment is carried out but the electrochemical polishing is omitted after nitriding, the chemical polishing time must be increased by about 2 to 3 seconds in order to remove the compound layer 10 (taking the abovementioned three-acid system polishing solution and temperature range as an example); the total removed thickness of both inner and outer walls is about 15 μm, but the surface roughness is slightly worse than that by the two-step polishing treatment. However, the long-duration single-step chemical polishing will result in unfavorable results as shown in FIGS. 9 to 11. Generally, the engraved vascular stent contains some roundabout fine patterns. FIG. 9 is a schematic view of a section of U-shaped supporting strut of the vascular stent before polishing treatment, and a U-shaped clearance formed by a narrow bending part 101 may be as small as 200 μm. The acidity obtained after anhydrous acetic acid and perchloric acid are mixed is not very strong, and the electrochemical polishing process at room temperature is relatively moderate. The clearance at the narrow bending part 101 will also remain subjected to substantially uniform isotropic corrosion even if the electrochemical polishing time is a little longer. After being subjected to continuous electrochemical polishing for 60 seconds, the supporting strut of the vascular stent becomes thin, but the contour of the narrow bending part 101 deforms less, as shown in FIG. 10. When the electrochemical polishing time is prolonged to 150 seconds, the local deformation is not significant. Meanwhile the chemical polishing solution is a strong acid system generally and has an extremely strong corrosivity at higher temperature. Therefore the chemical polishing process is usually more intense than the electrochemical polishing. In the heated chemical polishing process, a nitrogen oxide gas will be rapidly generated on the metal surface, and a large number of rapidly expanding bubbles are formed in the polishing solution. A large number of bubbles are also gathered in the vicinity of the narrow bending part 101, and theses bubbles cannot easily overflow from the clearance. The bubbles break in the clearance after expanding and mutually colliding. There are a large number of bubbles which continuously break to generate continuous dramatic impact on the narrow bending part 101, resulting in an additional impact corrosion in the clearance. When the chemical polishing time is too long, the impact corrosion caused by bubbles gathering will be severe; as a result, the narrow bending part 101 is non-homogeneously corroded. For example, after the chemical polishing has lasted for 4 to 6 seconds, the narrow bending part 101 has a contour as shown in FIG. 10. When the chemical polishing has lasted for more than 10 seconds, the narrow bending part 101 is apt to be severely deformed due to local excessive corrosion, as shown in FIG. 1I. The abovementioned two-step polishing treatment is applied, i.e., the first step is the easily controlled and more moderate electrochemical polishing, and the second step is the highly efficient chemical polishing within 8 seconds. The two-step polishing treatment is more favorable for preventing local deformation of the stent caused by local excessive corrosion compared with the single-step chemical polishing, and the polishing removal amount required by reaching a mirror polishing effect is also much smaller than the removal amount of the single-step electrochemical polishing.

In the embodiment, the wall thickness of the stent is 75 µm after the compound layer 50 is completely removed. It is reduced by 25 µm compared with the wall thickness of an original pure iron pipe, and the mass of the stent is about 12 mg. The cross section of the supporting strut of the stent (simplified as a round shape) is shown in FIG. 7, and the diffusion layer 10 and the solid solution layer 20 are sequentially arranged from outside to inside due to a surface nitriding effect under specific parameters.

The obtained diffusion layer 10 accounts for about 86.7%, the solid solution layer 20 accounts for about 13.3%, and the outer surface hardness of the diffusion layer 10 is 270 HV0.01; wherein the size of diffused second-phase particles is between 30 nm and 2 µm. In the embodiment, the electrochemical corrosion current density of the coronary stent in the simulated body fluid PBS is about 22 µA/cm², and is two times larger than 10 µA/cm² of pure iron. After the coronary stent is dilated by the balloon to 3 mm, the radial strength thereof is measured to be 142 kPa which is increased by 31.5% compared with 108 KPa of the radial strength of the pure iron stent with the same design and size. The solid solution layer 20 exhibits a very good inhibition effect on surface micro-crack propagation, and the effect is shown in FIG. 6. The size of second-phase particles in the diffusion layer 10 is preferably between 30 nm and 500 nm which can be controlled by reducing the stent temperature to about 470° C. reducing the flow ratio of hydrogen to nitrogen to 1:5 to 1:7, and maintaining the air pressure of about 55 Pa and the bias of about 600V during nitriding. Herein, the size of most of the second-phase particles is between 30 nm and 500 nm (the average size is also in the range), and the electrochemical corrosion current density on the surface of the stent can reach 26 µA/cm² or so. If the flow ratio of hydrogen to nitrogen is reduced to 1:5, while the bias is increased to 650 to 750V alternatively the air pressure is increased to 65 to 70 Pa, the stent temperature is maintained between 470° C. and 500° C. and the nitriding time is maintained for 30 minutes, the nitriding current density is still maintained within a range of 0.5 to 0.8 mA/cm²; accordingly, a structure and a property effect similar to FIG. 7 are obtained. Alternatively, if the flow ratio of hydrogen to nitrogen is reduced to 1:7, while the bias is increased to 750 to 800V alternatively the air pressure is increased to 85 to 100 Pa; a structure and a property effect similar to FIG. 7 are also obtained. By the method provided by the embodiment, the cross section of the supporting strut as shown in FIG. 7 is obtained; wherein the solid solution layer 20 preferably accounts for 10% to 25% of the total thickness (or radius of supporting strut), and the diffusion layer 10 accounts for 75% to 90% of the total thickness; thus the initial corrosion rate, fatigue resistance and radial strength of the stent can be obviously optimized, especially the former two properties.

Embodiment 3

The corresponding steps described in embodiment 1 are adopted to produce the same pure iron vascular stent, and the pure iron vascular stent is subjected to ion nitriding treatment after being cleaned. In the embodiment, the ion nitriding treatment equipment and a part of parameters are the same as those of embodiment 1, and the parameters different from embodiment 1 are set as follows: the nitriding temperature maintained at 470 to 500° C., the nitriding time being 60 minutes, and the thickness of the compound layer 50 formed on the surface of the stent being 3 to 4 µm. After subjected to nitriding treatment, the stent is further subjected to polishing treatment in order to completely remove the compound layer 50 so as to ensure that the stent surface is smooth and clean. The polishing treatment step described in embodiment 1 is applied, but just the polishing time is prolonged by 10 seconds so as to uniformly remove the thickness of the stent by about 50 µm, and the surface roughness also reaches 0.01 µm below.

Figure 8:
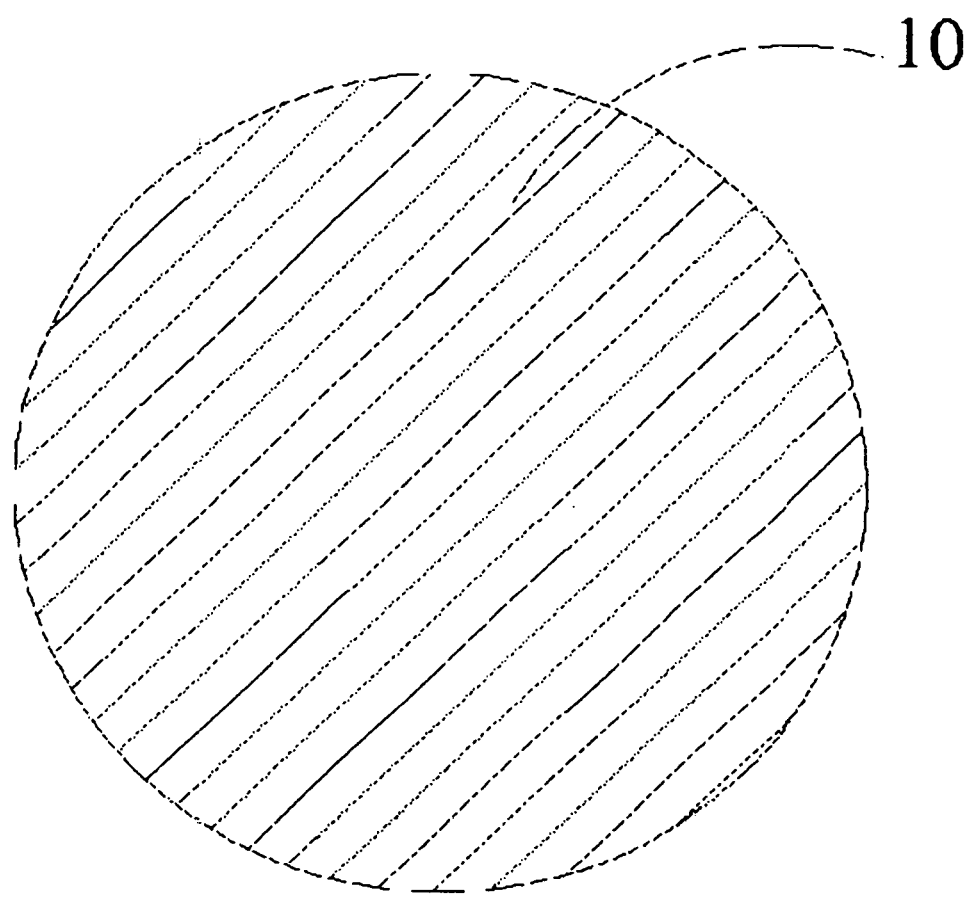
FIG. 8 is a schematic sectional view of a supporting strut of another vascular stent obtained by long-time nitriding treatment.

In the embodiment, after cleaning, nitriding, and polishing with the compound layer 50 completely removed, the wall thickness of the stent is 165 µm which is reduced by 55 µm compared with the wall thickness of the original pure iron pipe. The cross section (simplified as a round shape) of the supporting strut of the stent is shown in FIG. 8. As the nitriding treatment lasts longer than that of embodiment 1, a large number of nitrogen atoms are diffused to a deepest part inside the iron substrate, the iron substrates all become nitrogen-containing saturated solid solutions, the second phase is precipitated from the saturated solid solutions due to excessive nitrogen atoms, and the second-phase particles have been diffused to all regions of the saturated solid solutions; therefore, only the diffusion layer 10 remains in the cross section of the supporting strut. The surface microhardness of the diffusion layer 10 obtained in the embodiment is about 270 HV0.01. Meanwhile, there are different nitrogen atom concentrations at different depths of the diffusion layer 10 from the surface, the nitrogen atom concentrations are gradually decreased from outside to inside, the central region of the diffusion layer 10 had a minimum concentration value of nitrogen atoms and thus the micro-hardness here is about 230 HV0.01 which is still increased by 60 HV0.01 compared with the micro-hardness of the pure iron pipe. In view of the diffusion layer 10 having a higher hardness, the radial strength of the stent is measured to be about 65 kPa after the stent in the embodiment is dilated by the balloon to 12 mm, and the radial strength of the pure iron stent with the same shape and size (165 µm of wall thickness) is 40 kPa; thus the radial strength is increased by more than 60%. The region, nearby the surface, of the diffusion layer 10 has the characteristics of a high hardness and a poor plasticity, and the central region of the diffusion layer 10 has a slightly low hardness but a better plasticity (slightly worse than that of a pure iron material); therefore, the stent provided by the embodiment still has a better fatigue resistance; that is, such stent has inhibition effects on micro-crack initiation and inward micro-crack propagation which has been clearly described in embodiment 1. In the embodiment, the size of second-phase particles in the diffusion layer 10 is between 30 nm and 2 µm, and the electrochemical corrosion current density of the diffusion layer 10 in the simulated body fluid PBS is about 15 μA/cm² which is increased by about 50% compared with 10 μA/cm² of pure iron. Preferably, when the stent temperature is reduced to 470° C. and the flow ratio of nitrogen to hydrogen is reduced to 1:5 to 1:7 during nitriding, the size of second-phase particles is basically in the preferable range of 30 nm to 500 nm. The galvanic corrosion of the diffusion layer 10 in the in-vivo environment can be obviously accelerated in the preferable range, and the electrochemical corrosion current density of the diffusion layer 10 in the simulated body fluid PBS is about 18 μA/cm².

In the embodiment, the whole stent is composed exclusively of the diffusion layer 10; that is to say, each part (including an inner part) of the stent has a higher nitrogen content, and the hardness of inside of the supporting strut is greater than that of the supporting strut in embodiment 1; accordingly the overall strength of the stent is greatly improved, and the stent has the advantage that it is prone to galvanic corrosion on the whole. In summary, the embodiment is most favorable for improving the radial strength of the stent and shortening the time required by absorbing the stent; meanwhile, the fatigue resistance and smaller wall thickness are also ensured, thus the stent has better comprehensive properties.

Embodiment 4

The corresponding steps described in embodiment 2 are adopted to prepare the same pure iron vascular stent and the pure iron vascular stent is subjected to ion nitriding treatment after being cleaned. In the embodiment, the ion nitriding treatment equipment and a part of the parameters are the same as those of embodiment 2, and the parameters different from embodiment 1 are set as follows: the nitriding temperature maintained at 450 to 480° C. the nitriding time being 60 minutes, and the thickness of the compound layer 50 formed on the surface of the stent being 3 to 4 μm.

After subjected to nitriding treatment, the stent is further subjected to polishing treatment in order to completely remove the compound layer 50, and ensure that the stent surface is smooth and clean. The two-step polishing treatment step described in embodiment 2 is adopted. In view of the electrochemical polishing treatment time being easier to be precisely controlled, just the electrochemical polishing time is prolonged by 15 seconds so as to uniformly remove the thickness of about 25 μm of the stent, and the surface roughness also reaches 0.01 μm below.

In the embodiment, after cleaning, nitriding and polishing, the wall thickness of the stent is 70 μm which is reduced by 30 μm compared with the wall thickness of the original pure iron pipe. The cross section (simplified as a round shape) of the supporting strut of the stent is shown in FIG. 8. As such nitriding treatment lasts longer than that of the embodiment 2, a large number of nitrogen atoms have reached a deepest part inside the iron substrate, all of the iron substrates become nitrogen-containing saturated solid solutions, and the second-phase particles have been diffused throughout all regions of the saturated solid solutions; therefore, only the diffusion layer 10 remains in the cross section of the supporting strut. The diffusion layer 10 obtained by the embodiment has the following characteristics: a nitrogen atom concentration gradient existing at all various depths of the diffusion layer 10 from the surface, the surface Vickers micro-hardness of the diffusion layer 10 being 280 HV0.01 or so, the central region of the diffusion layer 10 having a minimum concentration of nitrogen atoms where the micro-hardness is about 230 HV0.01 (still increased by 60 HV0.01 compared with the micro-hardness of the pure iron pipe). Therefore, the stent in the embodiment still has a better fatigue resistance that is, an inhibition effect on surface micro-crack initiation and inward micro-crack propagation, which has been clearly described in the abovementioned embodiments. The radial strength of the stent is measured to be 140 kPa after the stent is dilated by the balloon to 3 mm, and the radial strength is increased by 73.9% compared with that of 92 kPa of the pure iron stent with the same shape and size (70 μm of wall thickness). The size of second-phase particles in the diffusion layer of the stent is between 30 nm and 2 μm, and the electrochemical corrosion current density of the stent with the such characterized structure in the simulated body fluid PBS is 15 μA/cm² or so which is increased by about 50% compared with 10 μA/cm² of pure iron. The size of second-phase particles can be controlled in the preferable range of 30 nm to 500 nm by reducing the stent temperature to 450° C. and reducing the flow ratio of nitrogen to hydrogen to 1:5 to 1:7 during nitriding; herein, the electrochemical corrosion current density of the stent in the simulated body fluid PBS can be increased to 18 μA/cm² or so. In the embodiment, under the premise that the temperature is maintained between 450° C. and 480° C. and the nitriding time is 60 minutes, the flow ratio of nitrogen to hydrogen may be reduced to 1:5, while the bias is being increased to 700 to 750V alternatively the air pressure is being increased to 70 to 75 Pa; alternatively, the flow ratio of nitrogen to hydrogen can be reduced to 1:7, while the bias is being increased to 750 to 800V alternatively the air pressure is being increased to 90 to 100 Pa; as a result, the nitriding current density is still maintained in a range between 0.5 mA/cm² and 0.8 mA/cm²; accordingly, a structure and a property effect similar to those obtained after the abovementioned nitriding treatment can be still obtained.

In summary, the embodiment is more favorable for improving the radial strength of the stent and shortening the time required by absorbing the stent compared with embodiment 2. Meanwhile it also ensures the fatigue resistance and the smaller wall thickness, and has better comprehensive properties.

Embodiment 5

The corresponding steps described in embodiment 1 are adopted to produce the same pure iron vascular stent and the pure iron vascular stent is subjected to ion nitriding treatment after being cleaned. In the embodiment, the ion nitriding treatment equipment and a part of the parameters are the same as those of embodiment 1, and the parameters different from embodiment 1 are set as follows: the nitriding stent temperature being maintained at 450 to 470° C., the nitriding time being 120 minutes, and the thickness of the compound layer 50 formed on the surface of the stent is about 5 μm.

After subjected to nitriding treatment, the stent is further subjected to polishing treatment in order to completely remove the compound layer 50, and to ensure that the stent surface is smooth and clean. The polishing treatment step described in embodiment 1 is applied, but the polishing time is prolonged by 20 seconds so as to uniformly remove the thickness of about 55 μm of the stent. The surface roughness Ra of the stent also reaches 0.01 μm below.

In the embodiment, after being cleaned, nitrided and polished, the wall thickness of the stent is 160 μm, which is reduced by 60 μm compared with the wall thickness of the original pure iron pipe. The cross section (simplified as a round shape) of the supporting strut of the stent is shown in FIG. 8. Because the nitriding process has been thoroughly carried out, a large number of nitrogen atoms have reached the deepest part inside the iron substrate. The concentration distribution of nitrogen atoms in the diffusion layer 10 is substantially uniform, and the second-phase particles have been uniformly distributed in all regions of the diffusion layer 10; that is to say, only the more uniform diffusion layer 10 is left in the cross section of the supporting strut. The micro-hardness of each region of the diffusion layer 10 obtained by the embodiment is substantially in a range of between 280 HV0.01 and 310 HV0.01, which has a very good inhibition effect on micro-crack initiation. In the embodiment, the radial strength of the obtained stent is measured to be 65 kPa after the stent is dilated by the balloon to 12 mm, which is increased by more than 80% compared with the radial strength of 35 kPa of the pure iron stent with the same shape and size (160 μm of wall thickness). The size of second-phase particles in the diffusion layer 10 obtained under such nitriding process conditions is substantially in a range of 30 nm to 2 μm; however, as subjected to 2-hour long-time nitriding, the nitrogen content of the diffusion layer 10 is rather high (weight percentage of 2.7% to 3.7%), the hardness is also rather high, the second phases therein agglomerate and grow, and the size concentrates in a range of 1 μm and 2 μm; thus the cathode area of micro galvanic corrosion is reduced. Meanwhile, the long-time nitriding may anneal the stent to a certain extent; the distorted and disordered grain boundaries, high residual stress and dislocation density which are originally brought out by cold working such as drawing are reduced to a certain extent or even completely restored, and thus the effect that the corrosion rate is accelerated by original structures is eliminated; therefore the corrosion rate is less than that of the diffusion layer 10 with a hardness value of 280 HV0.01 instead. During experimentation, the electrochemical corrosion current density of the stent in the simulated body fluid PBS is measured to be about 12 μA/cm$^2$ which is slightly increased compared with 10 μA/cm$^2$ of pure iron. Since the whole stent is exclusively composed of the more uniform diffusion layer 10 which is easier to be subjected to galvanic corrosion than the non-nitrided pure iron; therefore, the overall corrosion rate of the stent can be improved. In summary, under the premise that the wall thickness is reduced as much as possible, the embodiment is most favorable for improving the radial strength of the stent, and shortening the time required by absorbing the stent to a certain extent.

Embodiment 6

The corresponding steps described in embodiment 2 are adopted to produce the same pure iron vascular stent, and the pure iron vascular stent is subjected to ion nitriding treatment after being cleaned. In the embodiment, the ion nitriding treatment equipment and a part of the parameters are the same as those of embodiment 2, and the parameters different from embodiment 2 are set as follows: the nitriding stent temperature maintained 430 to 450° C. is, the nitriding time being 120 minutes, and the thickness of the compound layer 50 formed on the surface of the stent being about 5 μm.

After subjected to nitriding treatment, the stent is further subjected to polishing treatment in order to completely remove the compound layer 50 and to ensure that the stent surface is smooth and clean. The two-step polishing method described in embodiment 2 is applied, but the electrochemistry polishing time is prolonged by 30 seconds so as to uniformly remove the thickness of about 30 μm of the stent; the surface roughness Ra of the stent also reaches 0.01 μm below.

In the embodiment, after being cleaned, nitrided and polished, the wall thickness of the stent is 65 μm which is reduced by 35 μm compared with the wall thickness of the original pure iron pipe. The cross section (simplified as a round shape) of the supporting strut of the stent is shown in FIG. 8. Because the nitriding process has been thoroughly carried out a large number of nitrogen atoms have reached the deepest part inside the iron substrate. The concentration distribution of nitrogen atoms in the diffusion layer 10 is substantially uniform, and the second-phase particles have been more uniformly distributed in all regions of the diffusion layer 10; that is to say, only the diffusion layer 10 is left in the cross section of the supporting strut. The micro-hardness of each region of the diffusion layer 10 obtained in the embodiment is substantially in a range of between 290 HV0.01 and 320 HV0.01, which has a very good inhibition effect on micro-crack initiation. In the embodiment, after the stent is dilated by the balloon to 3 mm, the radial strength of the obtained stent is measured to be 135 kPa which is increased by 100% compared with the radial strength of 68 kPa of the pure iron stent with the same shape and size (65 μm of wall thickness). The size of second-phase particles in the diffusion layer 10 obtained under such nitriding process conditions is substantially in a range of 30 nm to 2 μm, and the corrosion rate is less than that of the diffusion layer 10 with a hardness value of 280 HV0.01 below, which has been clearly described in the embodiment 5. The electrochemical corrosion current density of the stent in the simulated body fluid PBS is experimentally measured to be 12 μA/cm$^2$ or so, which is slightly increased compared with 10 μA/cm$^2$ of pure iron. Similarly, the preferable process in the embodiment 4 can be adopted, accordingly, the size of second-phase particles is substantially in a preferable range of 30 nm to 500 nm and the electrochemical corrosion current density of the obtained diffusion layer 10 can be increased to about 15 μA/cm$^2$. Since the whole stent is exclusively composed of the more uniform diffusion layer 10 and the diffusion layer 10 is easier to be subjected to galvanic corrosion than the non-nitrided pure iron, the overall corrosion rate of the stent can be improved. In summary, under the premise that the wall thickness is reduced as much as possible, the embodiment is most favorable for improving the radial strength of the stent, and shortening the time required by absorbing the stent to a certain extent; and thus is suitable for a thin-walled absorbable coronary stent requiring very high radial strength.

In the present invention, after subjected to nitriding, the iron-based implantable medical device or component thereof (e.g., a supporting strut of a stent) may have a cross section as shown in one of FIG. 5. FIG. 7 and FIG. 8; wherein a layered structure of the device may have the preferred relative thickness (measured from the center to outside), thus an effect of being hard outside and ductile inside is most favorably generated. The diffusion layer 10 with a higher hardness helps to improve the structural strength, and the core layer 30 and the solid solution layer 20 both with very good plasticity can improve the fatigue resistance. In the method of the present invention, the concentration distribution and diffusion degree of nitrogen atoms in the iron substrate can be controlled, so as to realize the preferable thicknesses of the diffusion layer 10 and the solid solution layer 20 respectively; so that the solid solution layer 20 with a certain thickness, even together with the core layer 30 can be reserved inside the supporting strut of the stent for improving the plasticity of the supporting strut of the stent. Furthermore, under the premise of not reducing the radial strength of the stent, the nitrided stent can have a smaller wall thickness, such as a coronary stent with a wall thickness of 60 to 75 μm, a relative small peripheral stent with a wall thickness of 120 to 130 μm, and a relatively large peripheral stent with a wall thickness of 160 to 170 μm. For the thin-walled stent, not only the flexibility of the stent and the bending property thereof in complex lesion blood vessels can be improved; but also the entire corrosion cycle of the bioabsorbable stent can be shortened, the metal amount of the stent can be reduced, and further the local accumulation of iron ions in tissues can be reduced; the total mass of such a stent is 5 to 100 mg or so. The maximum wall thickness of the vascular stent can reach 300 μm. Both the mechanical properties and the corrosion rate of thick-walled stent can be considered and optimized in the present invention.

Several kinds of multi-layer structures provided by the present invention can be applied to a coronary stent, a peripheral stent and a non-vascular stent, or other implantable medical devices containing absorbable components. The selected original pipe material is pure iron or iron alloys containing more than 99% by mass of iron. Based on the treatment method provided by the present invention, the thickness of the pure iron or iron alloy prefabricated component should be 10 to 100 μm larger than the corresponding thickness of the corresponding component of the product. The thickness of the prefabricated component is more than 10 μm larger than the thickness of the absorbable component. Since the compound layer 50 is formed on the surface of the prefabricated component during nitriding, the nitrided prefabricated component is subjected to electrochemical or chemical polishing treatment; at least 5 μm thick surface (including the whole compound layer 50 and a small amount of diffusion layer 10) of the prefabricated component shall be removed, and the thickness is generally reduced by 20 to 60 μm.

The present invention focuses on optimization of a multi-layer structure property as well as a preparation method of an absorbable iron-based medical device or an absorbable component thereof, particularly for an absorbable vascular stent. Under the premise of ensuring the radial strength of the stent, the wall thickness of the iron-based stent is reduced, the corrosion rate and flexibility of the stent are both improved, and the multi-layer structure has a wider adaptability. Because interventional medical devices, especially stent products, have two conflicting factors of flexibility and strength, both the flexibility and the strength should be reasonably taken into consideration according to the characteristics and treatment requirements of lesion parts. A vascular stent is taken as an example, in practical clinical application; the lesion blood vessels have complicated variety, and have different requirements for the flexibility and the radial strength of the vascular stent. A severely calcified lesion vascular segment requires a higher-radial-strength stent; however, a higher-flexibility stent will be more suitable for a complex bending vascular segment. Meanwhile, for an absorbable iron-based medical device, the corrosion degradation property is also one of the most critical properties. The corrosion degradation property and other properties need be mutually reconciled so that the comprehensive property of the medical device is more targetedly adapted to a certain particular clinical symptom; therefore the present invention provides the multi-layer structures of the absorbable iron-based medical device, which can meet different application needs, as shown in FIG. 5, FIG. 7 or FIG. 8.

The present invention provides a treatment method for subjecting a bioabsorbable iron-based medical device to ion nitriding and polishing treatment. To prevent the nitrided compound layer from extending to inside of the iron-based material in a dendritic or flaky shape, a relative low stent temperature can be selected during nitriding, such as below 550° C. To prevent the generation of a thicker compound layer, the bias is preferably above 600V during nitriding. Different internal material structures of the iron-based device can be obtained by different implementation methods of surface nitriding treatment steps. A stent is taken as an example; the nitriding process parameters are adjusted in the abovementioned range, then the stent is subjected to the subsequent treatment step, the cross section of the supporting strut of the stent has a structure shown in one of FIG. 5, FIG. 7 and FIG. 8, and the proportion of each layer reaches an optimized range; wherein the preferable size of the second-phase particles in the diffusion layer 10 is between 30 nm and 500 nm, the micro-hardness of the diffusion layer 10 is in a preferably range of 220 to 320 HV0.01, and the nitrogen content of the diffusion layer is preferably 1.0 to 3.7 wt-%, so that the galvanic corrosion of the absorbable iron-based component in the in vivo environment can be significantly speeded up and the electrochemical corrosion rate is two times higher than that of a pure iron material before being treated by the method of the present invention.

In the prior art, the electrochemical polishing adopted after nitriding has significant disadvantages that a relative smooth and bright surface can only be obtained when the removal amount of the wall thickness of the stent reaches 40 μm, and the polished surface roughness can only be controlled below 0.1 μm. In order to improve the effect of the polishing treatment, an improvement on the polishing process after pure iron nitriding is performed in the present invention, and the two-step polishing step is provided for a thin-walled stent (original wall thickness≤100 μm): by means of such method, when the removal amount of the wall thickness of the supporting strut reaches 20 μm, it can be realized that the surface roughness of both inner and outer surfaces of the stent is to be 0.01 μm below, and a mirror bright similar effect is obtained.

Compared with the prior art, the bioabsorbable medical device or medical device component provided by the present invention has the following advantages.

1. The absorbable component of the bioabsorbable medical device is provided with a multi-layer structure internally. An absorbable stent is taken as an example; the mutually contradictory characteristics of corrosion rate, radial strength, flexibility, and wall thickness of the stent can achieve a relatively perfect balance point. The technical solution of the present invention also provides a preparation method of the absorbable medical device, and determines preferred process parameters and corresponding property effects.

2. By using preferred mixed gas flow ratio, air pressure, component temperature, bias, nitriding time and component temperature, the internal structure of the component can be controlled, and the thickness of the compound layer on the surface of the component is below 5 μm. Such compound layer can be completely removed by a preferred electrochemical or chemical polishing treatment. Both the inner and outer surfaces of the component can achieve a mirror bright effect just by a low polishing removal amount, and finally, the absorbable components with different internal structures can be obtained;

3. The optimized nitriding process and polishing process provided by the present invention can ensure that, with the same stent grid design and wall thickness, the absorbable iron-based vascular stent (the stent wall thickness can be reduced to 60 μm) has a supporting force comparable with that of a cobalt-chromium alloy stent. Both coronary stents and peripheral stents can achieve such effect; the radial strength of the stent is increased by 31.5% to 94.4% compared with that of a pure iron stent.

4. The present invention provides a bioabsorbable medical device or medical device component. The absorbable iron-based vascular stent is taken as an example; it comprises a multi-layer structure with a gradient property, and the multi-layer structure includes the diffusion layer, the solid solution layer and the core layer. As a result, the supporting force and flexibility of the stent can be simultaneously improved, and the corrosion resistance is reduced; the incidence of fatigue cracks in the surface can be reduced, and the propagation of surface microcracks to the inside of metal can also be inhibited, so that the absorbable medical device has a higher fatigue fracture resistant property in the early period when the absorbable medical device is implanted in the human body. After the pure iron component is subjected to surface nitriding, it has a high strength and a high hardness because of the strengthening effect of second-phase particles in the diffusion layer, so that the supporting property of the stent can be effectively improved. The solid solution layer and the core layer keep a higher elongation and a good plasticity similar to pure iron. Because most of the fatigue cracks are firstly formed on the metal surface, the fatigue crack initiation can be prevented by improving the component surface hardness and refining grains. On the other hand, the improvement on the plasticity of inside of the component will help to inhibit crack propagation; therefore, the propagation of cracks to inside of the component can be effectively inhibited by reserving the solid solution layer or core layer with a lower hardness inside the component:

5. The corrosion rate of the bioabsorbable medical device or medical device component can be increased by one time or so compared with that of a pure iron medical device, and the corrosion rate thereof in the simulated body fluid PBS can be increased by 180% compared with that of pure iron. When the outer surface hardness of the diffusion layer is controlled between 230 HV0.01 and 270 HV0.01, the finer the second-phase particles in the diffusion layer are, the faster the corrosion rate is; due to the presence of a certain number of second-phase particles in the diffusion layer, the material is easily subjected to galvanic corrosion when being subjected to normal corrosion, thereby shortening the time required by human body to absorb the medical device.

The above only describes the preferred embodiments of the present invention, and is not intended to limit the present invention. It will be appreciated that any modifications, equivalent alterations and improvements. etc. may be made within the spirit and principles of the present invention without departing from the scope of the invention.

What is claimed is:

1. A bioabsorbable medical device, comprising a medical device component, which comprises an absorbable component produced by subjecting a prefabricated component made from an iron-based raw material to ion nitriding treatment which is performed at an air pressure between 40 Pa and 150 Pa, a material composition inside the absorbable component changing with a depth from a surface, and characterized in that:

the absorbable component comprises at least a first part and a second part,
wherein the second part is surrounded by the first part, a hardness of the first part is higher than that of the second part,
an interface is formed between the first part and the second part, and cracks generated in the first part are obstructed by the interface when extending to the second part,
the first part comprising a dispersion layer comprising a first phase region and a granular-shaped second phase, and wherein the granular-shaped second phase diffusely distributes in the first phase region; and
wherein a thickness of the dispersion layer is 75% to 90% of a total thickness of the absorbable component.

2. The bioabsorbable medical device as set forth in claim 1, characterized in that the bioabsorbable medical device is an absorbable vascular stent, and the absorbable component comprises a plurality of struts connected to form a tubular grid; the vascular stent is produced by subjecting the iron based raw material with a uniform wall thickness to engraving and the ion nitriding treatment, and a wall thickness of the vascular stent is between 60 μm and 300 μm; under conditions of the same tubular grid and wall thickness, a radial strength of the vascular stent is increased by more than 30% compared with a radial strength of the non-nitrided vascular stent prefabricated by the iron-based raw material.

3. The bioabsorbable medical device as set forth in claim 2, characterized in that the vascular stent has a mass of between 5 mg and 100 mg.

4. The bioabsorbable medical device as set forth in claim 3, characterized in that the vascular stent wall thickness is between 60 μm and 100 μm or 160 μm and 170 μm.

5. The bioabsorbable medical device as set forth in claim 4, characterized in that a hardness of the vascular stent is between 280 HV and 320 HV; under the conditions of the same tubular grid and wall thickness, the radial strength of the vascular stent is increased by more than 80% compared with the radial strength of the non-nitrided vascular stent prefabricated by the iron-based raw material.

6. The bioabsorbable medical device as set forth in claim 1, characterized in that an electrochemical corrosion surface current density of the bioabsorbable medical device or medical device component is increased by more than 20% compared with an electrochemical corrosion surface current density of the non-nitrided iron-based raw material.

7. The bioabsorbable medical device as set forth in claim 1, wherein that the hardness of the dispersion layer is more than 220 HV and less than 280 HV and gradually decreases with the depth from the surface.

8. The bioabsorbable medical device as set forth in claim 1, wherein sizes of the second phase particles are between 30 nm and 500 nm.

9. The bioabsorbable medical device as set forth in claim 1, wherein the absorbable component is formed by the following steps:
forming a nitrogen-rich compound layer on the surface of the prefabricated component; and
completely removing the compound layer by an electrochemical polishing treatment so that only the dispersion layer remains on the surface of the prefabricated component.

10. The bioabsorbable medical device as set forth in claim 9, characterized in that a formula of an electrochemical polishing solution used in the electrochemical polishing treatment is as follows: anhydrous acetic acid and perchloric acid with a mass concentration of about 70% are uniformly mixed according to a volume ratio of 85 to 15, respectively.

11. The following bioabsorbable medical device as set forth in claim 10, characterized in that the electrochemical polishing solution is at a temperature of between 20 degrees centigrade and 25 degrees centigrade, a current of 2.8 A, and a voltage of 20 to 23V.

12. The bioabsorbable medical device as set forth in claim 1, wherein the ion nitriding treatment is performed with a flow ratio of nitrogen to hydrogen of 1:3.

13. The bioabsorbable medical device as set forth in claim 12, wherein the ion nitriding treatment is performed at a temperature of between 500° C. and 520° C., an air pressure of 60 Pa, and with a bias of about 600V.

14. The bioabsorbable medical device as set forth in claim 1, wherein air pressure during the ion nitriding treatment is between 50 Pa and 100 Pa.

15. A bioabsorbable medical device, which comprises a stent having a plurality of absorbable components produced by subjecting a prefabricated component made from an iron-based raw material to ion nitriding treatment which is performed at an air pressure between 40 Pa and 150 Pa, wherein each absorbable component is a strut having a core with a cross-section, a material composition inside each absorbable component changing with a depth from a surface, and characterized in that each absorbable component comprises:
  at least a first part and a second part, wherein the second part is surrounded by the first part, a hardness of the first part is higher than that of the second part, an interface is formed between the first part and the second part, and cracks generated in the first part are obstructed by the interface when extending to the second part; and
  the first part comprises a dispersion layer comprising a first phase region and a granular-shaped second phase, and wherein the granular-shaped second phase diffusely distributes in the first phase region, and wherein a thickness of the dispersion layer is 75% to 90% of a total thickness of the absorbable component.

16. The bioabsorbable medical device as set forth in claim 15, characterized in that the absorbable component is formed by the following steps:
  forming a nitrogen-rich compound layer on the surface of the prefabricated component; and
  completely removing the compound layer by an electrochemical polishing treatment so that only the dispersion layer remains on the surface of the prefabricated component.

17. The bioabsorbable medical device as set forth in claim 16, characterized in that the cross-section of the core is round, rectangular, trapezoidal, or oval.

18. The bioabsorbable medical device as set forth in claim 17, characterized in that both the first part and the interface are positioned inside the dispersion layer.

19. The bioabsorbable medical device as set forth in claim 17, characterized in that the hardness of the dispersion layer is more than 220 HV and less than 280 HV and gradually decreases with the depth from the surface.

20. The bioabsorbable medical device as set forth in claim 17, characterized in that sizes of the second phase particles are between 30 nm and 500 nm.

21. The bioabsorbable medical device as set forth in claim 16, characterized in that a formula of an electrochemical polishing solution used in the electrochemical polishing treatment is as follows: anhydrous acetic acid and perchloric acid with a mass concentration of about 70% are uniformly mixed according to a volume ratio of 85 to 15, respectively.

22. The following bioabsorbable medical device as set forth in claim 21, characterized in that the electrochemical polishing solution is at a temperature of between 20 degrees centigrade and 25 degrees centigrade, a current of 2.8 A, and a voltage of 20 to 23V.

23. A bioabsorbable medical device or medical device component, which comprises an absorbable component produced by subjecting a prefabricated component made from an iron-based raw material to ion nitriding treatment, a material composition inside the absorbable component changing with a depth from a surface, and characterized in that:
  the absorbable component comprises at least a first part and a second part,
  wherein the second part is surrounded by the first part, a hardness of the first part is higher than that of the second part,
  an interface is formed between the first part and the second part, and cracks generated in the first part are obstructed by the interface when extending to the second part,
  the first part comprising a dispersion layer comprising a first phase region and a granular-shaped second phase, and wherein the granular-shaped second phase diffusely distributes in the first phase region and comprises at least an α-phase ($Fe_{16}N_2$); and
  wherein a thickness of the dispersion layer is 75% to 90% of a total thickness of the absorbable component.

24. The bioabsorbable medical device or medical device component as set forth in claim 23, wherein the ion nitriding is performed at an air pressure between 40 Pa and 150 Pa.

* * * * *